(12) United States Patent
Parvulescu et al.

(10) Patent No.: US 11,691,932 B2
(45) Date of Patent: Jul. 4, 2023

(54) PROCESS FOR THE PREPARATION OF AN AROMATIC COMPOUND FROM BIOMASS

(71) Applicant: BASF SE, Ludwigshafen am Rhein (DE)

(72) Inventors: Andrei-Nicolae Parvulescu, Ludwigshafen (DE); Ulrich Mueller, Ludwigshafen (DE); Weiping Zhang, Dalian (CN)

(73) Assignee: BASF SE, Ludwigshafen (DE)

( * ) Notice: Subject to any disclaimer, the term of this patent is extended or adjusted under 35 U.S.C. 154(b) by 159 days.

(21) Appl. No.: 17/049,254

(22) PCT Filed: May 5, 2019

(86) PCT No.: PCT/CN2019/085492
§ 371 (c)(1),
(2) Date: Oct. 20, 2020

(87) PCT Pub. No.: WO2019/228132
PCT Pub. Date: Dec. 5, 2019

(65) Prior Publication Data
US 2021/0253495 A1  Aug. 19, 2021

(30) Foreign Application Priority Data
May 31, 2018 (WO) ................ PCT/CN2018/089142

(51) Int. Cl.
C07C 2/86 (2006.01)
B01J 29/74 (2006.01)
B01J 35/10 (2006.01)
B01J 37/10 (2006.01)

(52) U.S. Cl.
CPC .......... *C07C 2/862* (2013.01); *B01J 29/7415* (2013.01); *B01J 35/1019* (2013.01); *B01J 35/1023* (2013.01); *B01J 35/1038* (2013.01); *B01J 37/10* (2013.01); *C07C 2/86* (2013.01); *C07C 2/865* (2013.01); *C07C 2529/70* (2013.01)

(58) Field of Classification Search
CPC ....... Y02P 20/52; C07C 2529/70; C07C 2/86; C07C 2/862; C07C 2/865; B01J 29/7415; B01J 35/1019; B01J 35/1023; B01J 35/1038; B01J 37/10
USPC ........................................ 585/469, 471, 475
See application file for complete search history.

(56) References Cited

U.S. PATENT DOCUMENTS

2013/0245316 A1  9/2013  Masuno et al.
2014/0296600 A1  10/2014  Dauenhauer et al.

FOREIGN PATENT DOCUMENTS

WO  WO 2018/064604 A1  4/2018

OTHER PUBLICATIONS

Yilmaz, B. et al., "A new catalyst platform: zeolite Beta from template-free synthesis," Catalysis Science & Technology, May 2, 2013 vol. 3, No. 10, pp. 2580-2586 (total pp. 8).
Chang, C.C. et al., "Ultra-selective cycloaddition of dimethylfuran for renewable p-xylene with H-BEA," cited in Green Chemistry, 2014, vol. 16, Published/Accepted May 21, 2013, pp. 585-588.
Zhao, R.R. et al., "Excellent Performances of Dealuminated H-Beta Zeolites from Organotemplate-Free Synthesis in Conversion of Biomass-derived 2, 5-Dimethylfuran to Renewable p-Xylene," ChemSusChem, Oct. 17, 2018, vol. 11, pp. 3803-3811 (total pp. 22).
Ni, L. et al., "A Simple and Mild Approach for the Synthesis of p-Xylene from Bio-Based 2,5-Dimethyfuran by Using Metal Triflates," ChemSusChem, 2017, vol. 10, pp. 2394-2401.
Cho, H.J. et al., "Renewable p-Xylene from 2,5-Dimethylfuran and Ethylene Using Phosphorous-Containing Zeolite Catalysts," ChemCatChem, 2017, vol. 9, pp. 398-402.
International Search Report dated Aug. 8, 2019 in PCT/CN2019/085492 filed on Mary 5, 2019.
Zhigou Zhu et al., Applied Catalysis A: General, vol. 556, pp. 52-63.

*Primary Examiner* — Elizabeth D Wood
(74) *Attorney, Agent, or Firm* — Lowenstein Sandler LLP

(57) ABSTRACT

A process for the production of an aromatic compound which comprise reacting a mixture comprising ethylene and a furan compound over a zeolitic material having a BEA-type framework structure is described, wherein the zeolitic material having a BEA-type framework structure comprised in the catalyst is obtainable and/or obtained according to an organotemplate-free synthetic process.

15 Claims, 5 Drawing Sheets

PROCESS FOR THE PREPARATION OF AN AROMATIC COMPOUND FROM BIOMASS

TECHNICAL FIELD

The present invention relates to a process for the production of an aromatic compound comprising reacting a mixture comprising ethylene and a furan compound over a zeolitic material having a BEA-type framework structure, wherein the zeolitic material having a BEA-type framework structure comprised in the catalyst is obtainable and/or obtained according to an organotemplate-free synthetic process.

INTRODUCTION

The sustainable production of widely used bulk chemicals from biomass has received great attention due to the high cost, market volatility and impending depletion of petroleum-based feedstocks. p-Xylene (PX) is one of the most important specific chemicals of interest since it is extensively used to produce terephthalic acid (TA), polyethylene terephthalate (PET), and subsequent synthesis of polyester, synthetic fibers and plastic bottles, etc. A promising pathway for the production of renewable p-xylene, using Diels-Alder reaction between ethylene and 2,5-dimethylfuran (2,5-DMF) (see FIG. 1), have been proposed in recent years. In particular, both 2,5-DMF and ethylene can be derived from biomass, which offers a potential to reduce the dependence on petroleum for their production.

US 2013/0245316 A1 relates to a method for producing p-xylene from renewable sources and ethylene in the presence of a Lewis acid compounds as the catalyst. Ni, L. et al. *ChemSusChem* 2017, 10, 2394 concerns the synthesis of p-xylene from bio-based 2,5-dimethyfuran by using metal triflates. Chang, C.-C. et al. *Green Chem.* 2014, 16, 585 relate to the cycloaddition of biomass-derived ethylene and dimethylfuran with H-zeolite beta. Cho, H. J. et al. *ChemCatChem* 2017, 9, 398 concern to renewable p-xylene from 2,5-dimethylfuran and ethylene using a phosphorous-containing zeolite beta catalyst.

Although processes exist for the preparation of aromatic compounds from biomass exist, there remains the need for optimization of the conversion, in particular with regard to the activity and selectivity of the reaction.

DETAILED DESCRIPTION

It was the object of the present invention to provide an improved process for the preparation of aromatic compounds from biomass, and in particular an improved process for the reaction alkylenes with furan or alkylated derivatives thereof via Diels-Alder cycloaddition and subsequent elimination of water to the aromatic product. Thus, it has surprisingly been found that an improved process may be provided, in particular with regard to the activity and selectivity of the reaction, by employing a catalyst comprising a zeolitic material having a BEA-type framework structure as obtained from organotemplate-free synthesis.

Therefore, the present invention relates to a process for the production of an aromatic compound comprising:

(1) preparing a mixture (M1) comprising ethylene and a compound of formula (I)

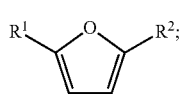

(2) feeding the mixture (M1) into a reactor containing a catalyst, said catalyst comprising a zeolitic material having a BEA-type framework structure;

(3) contacting the mixture (M1) with the catalyst in the reactor for reacting at least a portion of the mixture (M1) to an aromatic compound of formula (II)

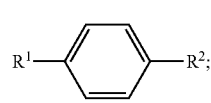

(4) collecting a reacted mixture (M2) containing the aromatic compound of formula (II) from the reactor;

wherein independently from one another $R^1$ and $R^2$ stand for H or for substituted or unsubstituted $(C_1-C_3)$alkyl, preferably for H or for substituted or unsubstituted $(C_1-C_2)$alkyl, more preferably for H or for substituted or unsubstituted methyl, and more preferably for H or for unsubstituted methyl, and wherein the zeolitic material having a BEA-type framework structure comprised in the catalyst is obtainable and/or obtained according to an organotemplate-free synthetic process.

As regards the physical and/or chemical properties, e. g. the XRD pattern, of the zeolitic material having a BEA-type framework structure comprised in the catalyst, no particular restriction applies. It is preferred that the zeolitic material having a BEA-type framework structure comprised in the catalyst displays an X-ray diffraction pattern comprising at least the following reflections:

| Intensity (%) | Diffraction angle 2 θ/° [Cu K(alpha 1)] |
|---|---|
| [12-32] | [21.79-21.99] |
| 100 | [22.28-22.48] |
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2θ range of the X-ray powder diffraction pattern, and wherein the BEA-type framework structure comprises $SiO_2$ and $X_2O_3$, wherein X is a trivalent element.

As disclosed above, $R^1$ and $R^2$ independently from one another stand for H or for substituted or unsubstituted $(C_1-C_3)$alkyl, preferably for H or for substituted or unsubstituted $(C_1-C_2)$alkyl, more preferably for H or for substituted or unsubstituted methyl, and more preferably for H or for unsubstituted methyl. It is preferred that $R^1$ and $R^2$ independently from one another stand for substituted or unsubstituted $(C_1-C_3)$alkyl, more preferably for substituted or unsubstituted $(C_1-C_2)$alkyl, more preferably for substituted or unsubstituted methyl, more preferably for unsubstituted methyl.

As regards $R^1$ and $R^2$, it is particularly preferred that $R^1$ stands for H and $R^2$ stands for substituted or unsubstituted $(C_1-C_3)$alkyl, more preferably for substituted or unsubstituted (C$_1$-C$_2$)alkyl, more preferably for substituted or unsubstituted methyl, and more preferably for unsubstituted methyl.

As disclosed above, the mixture (M1) comprises ethylene and a compound of formula (I)

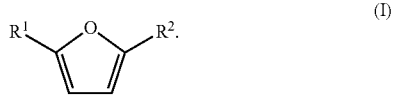

(I)

It is preferred that the compound of formula (I) is selected from the group consisting of substituted or unsubstituted furan, 2-methylfuran, 2,5-dimethylfuran, and mixtures of two or more thereof, more preferably from the group consisting of unsubstituted furan, 2-methylfuran, 2,5-dimethylfuran, and mixtures of two or more thereof, wherein more preferably the compound of formula (I) is 2-methylfuran and/or 2,5-dimethylfuran, preferably 2,5-dimethylfuran.

As regards the molar ratio of ethylene:compound of formula (I), no particular restriction applies. It is preferred that the molar ratio of ethylene:compound of formula (I) in the mixture (M1) prepared in (1) and reacted in (3) is in the range of from 0.01 to 1.5, more preferably from 0.05 to 1, more preferably from 0.08 to 0.7, more preferably from 0.1 to 0.5, more preferably from 0.12 to 0.3, more preferably from 0.14 to 0.2, and more preferably from 0.16 to 0.18.

Therefore, it is particularly preferred that the compound of formula (I) is selected from the group consisting of substituted or unsubstituted furan, 2-methylfuran, 2,5-dimethylfuran, and mixtures of two or more thereof, more preferably from the group consisting of unsubstituted furan, 2-methylfuran, 2,5-dimethylfuran, and mixtures of two or more thereof, wherein more preferably the compound of formula (I) is 2-methylfuran and/or 2,5-dimethylfuran, preferably 2,5-dimethylfuran, and that the molar ratio of ethylene:compound of formula (I) in the mixture (M1) prepared in (1) and reacted in (3) is in the range of from 0.01 to 1.5, more preferably from 0.05 to 1, more preferably from 0.08 to 0.7, more preferably from 0.1 to 0.5, more preferably from 0.12 to 0.3, more preferably from 0.14 to 0.2, and more preferably from 0.16 to 0.18.

As regards the mixture (M1) prepared in (1) and reacted in (3), no particular restriction applies such that further components may be included therein, e. g. water. It is preferred that the mixture (M1) prepared in (1) and reacted in (3) contains 5 wt.-% or less of water based on 100 wt. % of the compound of formula (I), more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of water based on 100 wt.-% of the compound of formula (I). It is particularly preferred that the mixture (M1) prepared in (1) and reacted in (3) is substantially free of water.

As disclosed above, no particular restriction applies as regards the mixture (M1) prepared in (1) and reacted in (3) such that further components may be included therein, e. g. a solvent system. It is preferred that the mixture (M1) prepared in (1) and reacted in (3) further comprises a solvent system, wherein the solvent system preferably comprises one or more solvents selected from the group consisting of butane, pentane, hexane, heptane, octane, nonane, decane, and mixtures of two or more thereof, more preferably from the group consisting of pentane, hexane, heptane, octane, nonane, and mixtures of two or more thereof, more preferably from the group consisting of hexane, heptane, octane, and mixtures of two or more thereof, wherein more preferably the solvent system comprises heptane, wherein more preferably the solvent system consists of heptane.

In the case where the mixture (M1) prepared in (1) and reacted in (3) further comprises a solvent system, it is preferred that the mixture (M1) prepared in (1) and reacted in (3) contains a solution of the compound of formula (I) in the solvent system, wherein the concentration of the compound of formula (I) in the solvent system is in the range of from 0.1 to 5 M, 0.5 to 3 M, more preferably from 1 to 2.5 M, more preferably from 1.3 to 2 M, more preferably from 1.4 to 1.7 M, and more preferably from 1.5 to 1.6 M.

Therefore, it is particularly preferred that the mixture (M1) prepared in (1) and reacted in (3) further comprises a solvent system, wherein the solvent system comprises one or more solvents selected from the group consisting of butane, pentane, hexane, heptane, octane, nonane, decane, and mixtures of two or more thereof, more preferably from the group consisting of pentane, hexane, heptane, octane, nonane, and mixtures of two or more thereof, more preferably from the group consisting of hexane, heptane, octane, and mixtures of two or more thereof, wherein more preferably the solvent system comprises heptane, wherein more preferably the solvent system consists of heptane, that the mixture (M1) prepared in (1) and reacted in (3) contains a solution of the compound of formula (I) in the solvent system, wherein the concentration of the compound of formula (I) in the solvent system is in the range of from 0.1 to 5 M, 0.5 to 3 M, more preferably from 1 to 2.5 M, more preferably from 1.3 to 2 M, more preferably from 1.4 to 1.7 M, and more preferably from 1.5 to 1.6 M, and that that the compound of formula (I) is selected from the group consisting of substituted or unsubstituted furan, 2-methylfuran, 2,5-dimethylfuran, and mixtures of two or more thereof, more preferably from the group consisting of unsubstituted furan, 2-methylfuran, 2,5-dimethylfuran, and mixtures of two or more thereof, wherein more preferably the compound of formula (I) is 2-methylfuran and/or 2,5-dimethylfuran, preferably 2,5-dimethylfuran.

As regards the partial pressure of ethylene in the reactor in which the mixture (M1) is fed in (2) and contacted with the catalyst in (3), no particular restriction applies. It is preferred that the partial pressure of ethylene in the reactor in which the mixture (M1) is fed in (2) and contacted with the catalyst in (3) is in the range of from 0.5 to 15 when measured at 25° C., more preferably from 0.5 to 15 MPa, more preferably from 1 to 10 MPa, more preferably from 2 to 8 MPa, more preferably from 2.5 to 6 MPa, more preferably from 3 to 5 MPa, and more preferably from 3.5 to 4.5 MPa.

As regards the origin of the compound of formula (I) and/or ethylene, no particular restriction applies such it may derive from a natural or synthetical process. It is preferred that the compound of formula (I) and/or ethylene, preferably the compound of formula (I) and ethylene are derived from biomass.

As disclosed above, no particular restriction applies as regards the zeolitic material having a BEA-type framework structure comprised in the catalyst. It is preferred that in (2) and (3) the zeolitic material comprised in the catalyst and having a BEA-type framework structure is in the H-form.

As disclosed above, no particular restriction applies as regards the zeolitic material having a BEA-type framework structure comprised in the catalyst such that further components may be comprised therein, e. g. one or more metals, preferably one or more alkali metals and an alkaline earth metals. It is preferred that in (2) and (3) the zeolitic material having a BEA-type framework structure comprised in the catalyst contains 5 wt.-% or less of a metal AM calculated as the element and based on 100 wt.-% of $SO_2$ contained in the framework structure of the zeolitic material having a BEA-type framework structure, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal AM calculated as the element and based on 100 wt.-% of $SiO_2$ contained in the framework structure of the zeolitic material having a BEA-type framework structure, wherein the metal AM stands for Na, preferably for Na and K, more preferably for alkali metals, and more preferably for alkali and alkaline earth metals.

As disclosed above, no particular restriction applies as regards the zeolitic material having a BEA-type framework structure comprised in the catalyst such that further components may be comprised therein, e. g. one or more metals, preferably one or more transition metals. It is preferred that in (2) and (3) the zeolitic material having a BEA-type framework structure comprised in the catalyst contains 5 wt.-% or less of a metal TM calculated as the element and based on 100 wt.-% of $SiO_2$ contained in the framework structure of the zeolitic material having a BEA-type framework structure, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal TM calculated as the element and based on 100 wt.-% of $SiO_2$ contained in the framework structure of the zeolitic material having a BEA-type framework structure, wherein the metal TM stands for Pt, Pd, Rh, and Ir, and preferably stands for transition metal elements of groups 3-12.

As regards the catalyst contained in the reactor, no particular restriction applies such that further components may be comprised therein, e. g. one or more metals, preferably one or more alkali metals and alkaline earth metals. It is preferred that in (2) and (3) the catalyst in the reactor contains 5 wt.-% or less of a metal AM calculated as the element and based on 100 wt.-% of the catalyst, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt. % or less, and more preferably 0.0001 wt.-% or less of a metal AM calculated as the element and based on 100 wt.-% of the catalyst, wherein the metal AM stands for Na, preferably for Na and K, more preferably for alkali metals, and more preferably for alkali and alkaline earth metals.

As disclosed above, no particular restriction applies as regards the catalyst contained in the reactor, such that further components may be comprised therein, e. g. one or more metals, preferably one or more transition metals. It is preferred that the catalyst contained in the reactor contains 5 wt.-% or less of a metal TM calculated as the element and based on 100 wt.-% of the catalyst, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal TM calculated as the element and based on 100 wt.-% of the catalyst, wherein the metal TM stands for Pt, Pd, Rh, and Ir, and preferably stands for transition metal elements of groups 3-12.

As disclosed above, no particular restriction applies as regards the zeolitic material having a BEA-type framework structure comprised in the catalyst such that further components may be comprised therein, e. g. phosphorous. It is preferred that in (2) and (3) the zeolitic material having a BEA-type framework structure comprised in the catalyst contains 5 wt. % or less of phosphorous calculated as the element and based on 100 wt.-% of $SiO_2$ contained in the framework structure of the zeolitic material having a BEA-type framework structure, more preferably 1 wt. % or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of phosphorous calculated as the element and based on 100 wt.-% of $SiO_2$ contained in the framework structure of the zeolitic material having a BEA-type framework structure.

As disclosed above, no particular restriction applies as regards the catalyst contained in the reactor such that further components may be comprised therein, e. g. phosphorous. It is preferred that in (2) and (3) the catalyst contains 5 wt. % or less of phosphorous calculated as the element and based on 100 wt.-% of the catalyst, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal AM calculated as the element and based on 100 wt.-% of the catalyst.

As regards the contacting of the mixture (M1) with the catalyst in (3), no particular restriction applies, such that any suitable conditions may be applied, e. g. in view of the temperature. It is preferred that the contacting of the mixture (M1) with the catalyst in (3) is conducted at a temperature in the range of from 150 to 350° C., more preferably from 200 to 330° C., more preferably from 230 to 320° C., more preferably from 250 to 315° C., more preferably from 270 to 310° C., more preferably from 280 to 305° C., and more preferably in the range of from 290 to 300° C.

As disclosed above, no particular restriction applies as regards the contacting of the mixture (M1) with the catalyst in (3) such that any suitable conditions may be applied, e. g. in view of the duration. It is preferred that the duration of the contacting of the mixture (M1) with the catalyst in (3) is in the range of from 0.5 to 70 h, more preferably from 1 to 50 h, more preferably from 3 to 40 h, more preferably from 5 to 35 h, more preferably from 10 to 30 h, more preferably from 15 to 25 h, more preferably from 18 to 23 h, and more preferably in the range of from 19 to 21 h.

Therefore, it is particularly preferred that the contacting of the mixture (M1) with the catalyst in (3) is conducted at a temperature in the range of from 150 to 350° C., more preferably from 200 to 330° C., more preferably from 230 to 320° C., more preferably from 250 to 315° C., more preferably from 270 to 310° C., more preferably from 280 to 305° C., and more preferably in the range of from 290 to 300° C., and that the duration of the contacting of the mixture (M1) with the catalyst in (3) is in the range of from 0.5 to 70 h, more preferably from 1 to 50 h, more preferably from 3 to 40 h, more preferably from 5 to 35 h, more preferably from 10 to 30 h, more preferably from 15 to 25 h, more preferably from 18 to 23 h, and more preferably in the range of from 19 to 21 h.

As disclosed above, no particular restriction applies as regards the contacting of the mixture (M1) with the catalyst in (3) and the collecting of the reacted mixture (M2) in (4) such that any suitable conditions may be applied, e. g. in view of the reaction mode. It is preferred that the contacting of the mixture (M1) with the catalyst in (3) and the collecting of the reacted mixture (M2) in (4) is conducted in a continuous mode and/or in a batch mode, more preferably in a batch mode.

As regards the reaction mode in which the process is conducted, no particular restriction applies. It is preferred that the process is conducted in a continuous mode and/or in a batch mode, preferably in a batch mode.

As disclosed above, the process for the production of an aromatic compound comprises steps (1), (2), (3), and (4). As regards said process, no particular restriction applies in view of the process steps such that further process steps may be comprised therein. It is preferred that the process further comprises:

(5) separating the compound of formula (II) from the reacted mixture (M2) for obtaining a mixture (M3) containing unreacted compound of formula (I) and/or unreacted ethylene.

In the case where the process comprises (5) as disclosed above, again no particular restriction applies in view of the process steps such that further process steps may be comprised therein. It is preferred that the process further comprises:

(6) recycling the mixture (M3) containing unreacted compound of formula (I) and/or unreacted ethylene to (1).

As disclosed above, no particular restriction applies as regards the zeolitic material having a BEA-type framework structure comprised in the catalyst. It is preferred that the zeolitic material having a BEA-type framework structure comprised in the catalyst displays a $SiO_2:X_2O_3$ molar ratio in the range of from 10 to 200, more preferably from 15 to 150, more preferably from 20 to 100, more preferably from 25 to 70, more preferably from 30 to 65, more preferably from 35 to 60, more preferably from 38 to 55, more preferably from 40 to 50, and more preferably from 42 to 46, wherein preferably the $SiO_2:X_2O_3$ molar ratio of the framework structure is determined from elemental analysis or from the $^{29}Si$ MAS NMR of the zeolitic material, preferably from the $^{29}Si$ MAS NMR of the zeolitic material. Preferably, the $SiO_2:X_2O_3$ molar ratio of the framework structure is determined by $^{29}Si$ MAS NMR according to the method described in the experimental section.

As regards the trivalent element X of the zeolitic material having a BEA-type framework structure comprised in the catalyst, no particular restriction applies. It is preferred that the trivalent element X of the zeolitic material having a BEA-type framework structure comprised in the catalyst is selected from the group consisting of Al, B, In, Ga, and a mixture of two or more thereof, more preferably from the group consisting of Al, Ga, and a mixture thereof, X more preferably being Al.

As disclosed above, no particular restriction applies as regards the zeolitic material having a BEA-type framework structure comprised in the catalyst. It is preferred that the zeolitic material having a BEA-type framework structure comprised in the catalyst displays an amount of Bronsted acid sites (BA) in the range of from 100 to 900 µmol/g, more preferably from 150 to 700 µmol/g, more preferably from 200 to 650 µmol/g, more preferably from 350 to 600 µmol/g, more preferably from 380 to 550 µmol/g, more preferably from 410 to 500 µmol/g, more preferably from 430 to 470 µmol/g, and more preferably from 445 to 450 µmol/g, wherein the amount of Bronsted acid sites is determined according to the temperature programmed desorption of ammonia (NH3-TPD) or according to $^{31}P$ MAS NMR using trimethylphosphine oxide. Preferably, the amount of Bronsted acid sites is determined according to the method described in the experimental section.

As disclosed above, no particular restriction applies as regards the zeolitic material having a BEA-type framework structure comprised in the catalyst. It is preferred that the zeolitic material having a BEA-type framework structure comprised in the catalyst displays an amount of Lewis acid sites (LA) in the range of from 100 to 350 µmol/g, more preferably from 110 to 300 µmol/g, more preferably from 120 to 280 µmol/g, more preferably from 140 to 260 µmol/g, more preferably from 150 to 240 µmol/g, more preferably from 160 to 220 µmol/g, more preferably from 170 to 200 µmol/g, and more preferably from 180 to 190 µmol/g, wherein the amount of Lewis acid sites is determined according to the temperature programmed desorption of ammonia (NH3-TPD) or according to $^{31}P$ MAS NMR using trimethylphosphine oxide. Preferably, the amount of Lewis acid sites is determined according to the method described in the experimental section.

Therefore, it is particularly preferred that that the zeolitic material having a BEA-type framework structure comprised in the catalyst displays an amount of Bronsted acid sites (BA) in the range of from 100 to 900 µmol/g, more preferably from 150 to 700 µmol/g, more preferably from 200 to 650 µmol/g, more preferably from 350 to 600 µmol/g, more preferably from 380 to 550 µmol/g, more preferably from 410 to 500 µmol/g, more preferably from 430 to 470 µmol/g, and more preferably from 445 to 450 µmol/g, wherein the amount of Bronsted acid sites is determined according to the temperature programmed desorption of ammonia (NH3-TPD) or according to $^{31}P$ MAS NMR using trimethylphosphine oxide, and that the zeolitic material having a BEA-type framework structure comprised in the catalyst displays an amount of Lewis acid sites (LA) in the range of from 100 to 350 µmol/g, more preferably from 110 to 300 µmol/g, more preferably from 120 to 280 µmol/g, more preferably from 140 to 260 µmol/g, more preferably from 150 to 240 µmol/g, more preferably from 160 to 220 µmol/g, more preferably from 170 to 200 µmol/g, and more preferably from 180 to 190 µmol/g, wherein the amount of Lewis acid sites is determined according to the temperature programmed desorption of ammonia (NH3-TPD) or according to $^{31}P$ MAS NMR using trimethylphosphine oxide.

Further, it is particularly preferred that the ratio BA:LA of the amount of Bronsted acid sites (BA) to the amount of Lewis acid sites (LA) displayed by the zeolitic material having a BEA-type framework structure comprised in the catalyst is in the range of from 0.5 to 8, preferably from 1 to 5, more preferably from 1.3 to 4, more preferably from 1.6 to 3.4, more preferably from 1.8 to 3, more preferably from 2.0 to 2.7, more preferably from 2.2 to 2.6, and more preferably from 2.3 to 2.5, wherein the amount of Bronsted and Lewis acid sites is respectively determined according to the temperature programmed desorption of ammonia (NH3-TPD) or according to $^{31}P$ MAS NMR using trimethylphosphine oxide.

As regards the physical and/or chemical properties, e. g. the BET surface area, of the zeolitic material having a BEA-type framework structure comprised in the catalyst, no particular restriction applies. It is preferred that the BET surface area of the zeolitic material having a BEA-type framework structure comprised in the catalyst as determined according to ISO 9277:2010 is in the range of from 350 to 800 m$^2$/g, more preferably from 400 to 700 m$^2$/g, more preferably from 430 to 650 m$^2$/g, more preferably from 450 to 600 m$^2$/g, more preferably from 460 to 550 m$^2$/g, more preferably from 470 to 530 m$^2$/g, more preferably from 480 to 520 m$^2$/g, and more preferably from 490 to 510 m$^2$/g.

As regards the physical and/or chemical properties, e. g. the total pore volume, of the zeolitic material having a BEA-type framework structure comprised in the catalyst, no particular restriction applies. It is preferred that the total pore volume of the zeolitic material having a BEA-type framework structure comprised in the catalyst as determined by nitrogen adsorption from the BJH method is in the range of from 0.3 to 0.5 cm$^3$/g, preferably from 0.31 to 0.45 cm$^3$/g, more preferably from 0.32 to 0.42 cm$^3$/g, more preferably from 0.33 to 0.4 cm$^3$/g, more preferably from 0.34 to 0.39 cm$^3$/g, more preferably from 0.35 to 0.38 cm$^3$/g, and more preferably from 0.36 to 0.37 cm$^3$/g, wherein the total pore volume is preferably determined according to DIN 66134.

As regards the organotemplate-free synthetic process according to which the zeolitic material having a BEA-type framework structure comprised in the catalyst is obtainable and/or obtained, no particular restriction applies. It is preferred that the organotemplate-free synthetic process comprises (A) preparing a mixture comprising one or more sources for SiO$_2$, one or more sources for X$_2$O$_3$, and seed crystals, the seed crystals comprising one or more zeolitic materials having a BEA-type framework structure;

(B) crystallizing the mixture obtained in (A) for obtaining a zeolitic material having a BEA-type framework structure;

wherein X is a trivalent element, and wherein the mixture prepared in (A) and crystallized in (B) does not contain an organotemplate as structure-directing agent.

In the case where the process comprises the organotemplate-free synthetic process including (A) and (B) as disclosed above, no particular restriction applies as regards the mixture prepared in (A) and crystallized in (B) such that further components, e. g. carbon, may be comprised therein. It is preferred that the mixture prepared in (A) and crystallized in (B) contains 5 wt.-% or less of carbon calculated as the element and based on 100 wt.-% of SiO$_2$ contained in the mixture, more preferably 1 wt.-% or less, more preferably 0.5 wt.-% or less, more preferably 0.1 wt. % or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of carbon calculated as the element and based on 100 wt.-% of SiO$_2$ contained in the mixture.

In the case where the process comprises the organotemplate-free synthetic process including (A) and (B) as disclosed above, no particular restriction applies as regards the zeolitic material having a BEA-type framework structure obtained in (B) such that further components may be comprised therein, e. g. one or more alkali metals M. It is preferred that the zeolitic material having a BEA-type framework structure obtained in (B) comprises one or more alkali metals M, wherein M is preferably selected from the group consisting of Li, Na, K, Cs, and combinations of two or more thereof, more preferably from the group consisting of Li, Na, K, and combinations of two or more thereof, wherein more preferably the alkali metal M is Na and/or K, more preferably Na.

In the case where the zeolitic material having a BEA-type framework structure obtained in (B) comprises one or more alkali metals M as disclosed above, no particular restriction applies as regards the molar ratio M:SiO$_2$ in the mixture prepared in (A) and crystallized in (B). It is preferred that the molar ratio M:SiO$_2$ in the mixture prepared in (A) and crystallized in (B) is in the range of from 0.05 to 5, more preferably from 0.1 to 2, more preferably from 0.3 to 1, more preferably from 0.4 to 0.8, more preferably from 0.45 to 0.7, more preferably from 0.5 to 0.65, and more preferably from 0.55 to 0.6.

In the case where the process comprises the organotemplate-free synthetic process including (A) and (B) as disclosed above, no particular restriction applies as regards the one or more sources for SiO$_2$ contained in the mixture prepared in (A) and crystallized in (B). It is preferred that the one or more sources for SiO$_2$ contained in the mixture prepared in (A) and crystallized in (B) comprises one or more silicates, preferably one or more alkali metal silicates, wherein the alkali metal is more preferably selected from the group consisting of Li, Na, K, Rb, and Cs, wherein more preferably the alkali metal is Na and/or K, and wherein more preferably the alkali metal is Na, wherein more preferably the one or more sources for SiO$_2$ contained in the mixture prepared in (A) and crystallized in (B) comprises water glass, preferably sodium and/or potassium silicate, more preferably sodium silicate.

In the case where the one or more sources for SiO$_2$ contained in the mixture prepared in (A) and crystallized in (B) comprises one or more silicates as disclosed above, no particular restriction applies in view of further components comprised therein. It is preferred that the one or more sources for SiO$_2$ contained in the mixture prepared in (A) and crystallized in (B) further comprises one or more silicas, more preferably one or more silica hydrosols and/or one or more colloidal silicas, and more preferably one or more colloidal silicas.

Therefore, it is particularly preferred that in the case where the process comprises the organotemplate-free synthetic process including (A) and (B) as disclosed above the the one or more sources for SiO$_2$ contained in the mixture prepared in (A) and crystallized in (B) comprises one or more silicates, preferably one or more alkali metal silicates, wherein the alkali metal is more preferably selected from the group consisting of Li, Na, K, Rb, and Cs, wherein more preferably the alkali metal is Na and/or K, and wherein more preferably the alkali metal is Na, wherein more preferably the one or more sources for SiO$_2$ contained in the mixture prepared in (A) and crystallized in (B) comprises water glass, preferably sodium and/or potassium silicate, more preferably sodium silicate, and that the one or more sources for SiO$_2$ contained in the mixture prepared in (A) and crystallized in (B) further comprises one or more silicas, more preferably one or more silica hydrosols and/or one or more colloidal silicas, and more preferably one or more colloidal silicas.

In the case where the process comprises the organotemplate-free synthetic process including (A) and (B) as disclosed above, no particular restriction applies as regards X as long as it is a trivalent element as disclosed above. It is preferred that X is selected from the group consisting of Al, B, In, Ga, and a mixture of two or more thereof, more preferably selected from the group consisting of Al, Ga, and a mixture thereof, X more preferably being Al.

In the case where the process comprises the organotemplate-free synthetic process including (A) and (B) as disclosed above, no particular restriction applies as regards the one or more sources for $X_2O_3$ contained in the mixture prepared in (A) and crystallized in (B). It is preferred that the one or more sources for $X_2O_3$ contained in the mixture prepared in (A) and crystallized in (B) comprises one or more aluminate salts, preferably an aluminate of an alkali metal, wherein the alkali metal is preferably selected from the group consisting of Li, Na, K, Rb, and Cs, wherein more preferably the alkali metal is Na and/or K, and wherein more preferably the alkali metal is Na.

In the case where the process comprises the organotemplate-free synthetic process including (A) and (B) as disclosed above, no particular restriction applies as regards the molar ratio $SiO_2:X_2O_3$ of the mixture prepared in (A) and crystallized in (B). It is preferred that the molar ratio $SiO_2:X_2O_3$ of the mixture prepared in (A) and crystallized in (B) is in the range of from 1 to 200, more preferably from 5 to 100, more preferably from 10 to 50, more preferably from 15 to 40, more preferably from 20 to 30, more preferably from 23 to 25, and more preferably from 23.5 to 24.

In the case where the process comprises the organotemplate-free synthetic process including (A) and (B) as disclosed above, no particular restriction applies as regards the mixture prepared in (A) and crystallized in (B) such that further components, e. g. one or more solvents, may be comprised therein. It is preferred that the mixture prepared in (A) and crystallized in (B) further comprises one or more solvents, wherein said one or more solvents more preferably comprises water, more preferably deionized water, wherein more preferably water is employed as the solvent further comprised in the mixture prepared in (A) and crystallized in (B), preferably deionized water.

In the case where the mixture prepared in (A) and crystallized in (B) further comprises one or more solvents as disclosed above, no particular restriction applies as regards the molar ratio $H_2O:SiO_2$ of the mixture prepared in (A) and crystallized in (B). It is preferred that the molar ratio $H_2O:SiO_2$ of the mixture prepared in (A) and crystallized in (B) is in the range of from 5 to 100, preferably from 10 to 50, more preferably from 13 to 30, more preferably from 15 to 20, and more preferably from 17 to 18.

In the case where the process comprises the organotemplate-free synthetic process including (A) and (B) as disclosed above, no particular restriction applies as regards the conditions, e. g. the temperature of the mixture, at which the crystallization in (B) is conducted. It is preferred that the crystallization in (B) involves heating of the mixture, more preferably at a temperature in the range of from 80 to 200° C., more preferably from 90 to 180° C., more preferably from 100 to 160° C., more preferably from 110 to 140° C., and more preferably from 115 to 130° C.

In the case where the process comprises the organotemplate-free synthetic process including (A) and (B) as disclosed above, no particular restriction applies as regards the conditions, e. g. the pressure, at which the crystallization in (B) is conducted. It is preferred that the crystallization in (B) is conducted under autogenous pressure, more preferably under solvothermal conditions, and more preferably under hydrothermal conditions.

Therefore, it is particularly preferred that the crystallization in (B) involves heating of the mixture, more preferably at a temperature in the range of from 80 to 200° C., more preferably from 90 to 180° C., more preferably from 100 to 160° C., more preferably from 110 to 140° C., and more preferably from 115 to 130° C., and that the crystallization in (B) is conducted under autogenous pressure, more preferably under solvothermal conditions, and more preferably under hydrothermal conditions.

In the case where the crystallization in (B) involves heating of the mixture as disclosed above and/or where the crystallization in (B) is conducted under autogenous pressure as disclosed above, no particular restriction applies as regards the period in which the mixture is heated in (B). It is preferred that in (B) the mixture is heated for a period in the range of from 5 to 200 h, preferably from 20 to 160 h, more preferably from 60 to 140 h, and more preferably from 100 to 130 h.

In the case where the process comprises the organotemplate-free synthetic process including (A) and (B) as disclosed above, no particular restriction applies as regards further process steps comprised therein. It is preferred that the organotemplate-free synthetic process for the preparation of the zeolitic material having a BEA-type framework structure further comprises (C) isolating the zeolitic material having a BEA-type framework structure obtained in (B), preferably by filtration; and (D) optionally washing the zeolitic material having a BEA-type framework structure obtained in (B) or (C), preferably in (C); and/or, (E) optionally drying the zeolitic material having a BEA-type framework structure obtained in (B), (C) or (D), preferably in (D);

wherein steps (C) and/or (D) and/or (E) can be conducted in any order, and wherein one or more of said steps is preferably repeated one or more times.

In the case where the process comprises the organotemplate-free synthetic process including (A), (B), (C), optionally (D), and optionally (E) as disclosed above, again no particular restriction applies as regards further process steps comprised therein. It is preferred that the organotemplate-free synthetic process for the preparation of the zeolitic material having a BEA-type framework structure further comprises (F) exchanging one or more of the ionic non-framework elements contained in the zeolitic material having a BEA-type framework structure obtained in (C), (D), or (E), preferably in (E), against $H^+$ and/or $NH_4^+$, preferably against $NH_4^+$; and/or, preferably and (G) drying and/or calcining, preferably drying and calcining the zeolitic material having a BEA-type framework structure obtained in (C), (D), (E), or (F);

wherein steps (F) and/or (G) is preferably repeated one or more times, preferably one to three times, more preferably once or twice, and more preferably once.

In the case where the process comprises the organotemplate-free synthetic process including (A), (B), (C), optionally (D), optionally (E), and optionally (F) and (G) as disclosed above, again no particular restriction applies as regards further process steps comprised therein. It is preferred that the organotemplate-free synthetic process for the preparation of the zeolitic material having a BEA-type framework structure further comprises (H) treating the zeolitic material having a BEA-type framework structure obtained in (C), (D), (E), (F), or (G), preferably in (G), with an aqueous solution having a pH of at most 5; and (I) isolating the zeolitic material having a BEA-type framework structure obtained in (H), preferably by filtration; and/or, (J) optionally washing the zeolitic material having a BEA-type framework structure obtained in (H) or (I), preferably in (I); and/or, (K) optionally drying and/or calcining, preferably drying the zeolitic material having a BEA-type framework structure obtained in (H), (I), or (J), preferably in (J);

wherein the steps (I) and/or (J) and/or (K) can be conducted in any order, and wherein one or more of said steps is preferably repeated one or more times, preferably one to three times, more preferably once or twice, and more preferably once.

In the case where the process comprises the organotemplate-free synthetic process including (H), (I), optionally (J), and optionally (K) as disclosed above, no particular restriction applies as regards the conditions, e. g. the pH, of the aqueous solution used for treating the zeolitic material in (H) as long as the aqueous solution having a pH of at most 5. It is preferred that the pH of the aqueous solution used for treating the zeolitic material in (H) has a pH in the range of from −1.5 to 3, preferably of from −1.2 to 2, more preferably of from −1 to 1.5, more preferably of from −0.8 to 1, more preferably of from −0.6 to 0.7, more preferably of from −0.5 to 0.5, more preferably of from −0.3 to 0.3, more preferably of from −0.2 to 0.2, and more preferably of from −0.1 to 0.1.

In the case where the process comprises the organotemplate-free synthetic process including (H), (I), optionally (J), and optionally (K) as disclosed above, no particular restriction applies as regards the nature of the aqueous solution with which the zeolitic material is treated in (H). It is preferred that in (H) the zeolitic material is treated with an aqueous solution of a mineral acid. Further, it is preferred that the concentration of the mineral acid in the aqueous solution is in the range of from 0.05 to 4 M, more preferably from 0.1 to 3 M, more preferably from 0.2 to 2.5 M, more preferably from 0.4 to 2 M, more preferably from 0.6 to 1.5 M, more preferably from 0.8 to 1.2 M, and more preferably from 0.9 to 1.1 M.

In the case where a mineral acid is used in (H) as disclosed above, no particular restriction applies as regards the nature of the mineral acid. It is preferred that the mineral acid is selected from the group consisting of HF, HCl, HBr, $HNO_3$, $H_3PO_4$, $H_2SO_4$, $H_3BO_3$, $HClO_4$, and mixtures of two or more thereof, more preferably from the group consisting of HCl, HBr, $HNO_3$, $H_2SO_4$, $HClO_4$, and mixtures of two or more thereof, more preferably from the group consisting of HCl, $HNO_3$, $H_2SO_4$, and mixtures of two or more thereof, wherein more preferably the mineral acid is HCl and/or $HNO_3$, preferably $HNO_3$.

Therefore, it is particularly preferred that in (H) the zeolitic material is treated with an aqueous solution of a mineral acid. Further, it is preferred that the concentration of the mineral acid in the aqueous solution is in the range of from 0.05 to 4 M, more preferably from 0.1 to 3 M, more preferably from 0.2 to 2.5 M, more preferably from 0.4 to 2 M, more preferably from 0.6 to 1.5 M, more preferably from 0.8 to 1.2 M, and more preferably from 0.9 to 1.1 M, and that the mineral acid is selected from the group consisting of HF, HCl, HBr, $HNO_3$, $H_3PO_4$, $H_2SO_4$, $H_3BO_3$, $HClO_4$, and mixtures of two or more thereof, more preferably from the group consisting of HCl, HBr, $HNO_3$, $H_2SO_4$, $HClO_4$, and mixtures of two or more thereof, more preferably from the group consisting of HCl, $HNO_3$, $H_2SO_4$, and mixtures of two or more thereof, wherein more preferably the mineral acid is HCl and/or $HNO_3$, preferably $HNO_3$.

In the case where the process comprises the organotemplate-free synthetic process including (H), (I), optionally (J), and optionally (K) as disclosed above, no particular restriction applies as regards the manner according to which the zeolitic material having a BEA-type framework structure obtained in (C), (D), (E), (F), or (G), preferably in (G), is treated with an aqueous solution having a pH of at most 5. According to a first alternative, it is preferred that in (H) the zeolitic material is added to the aqueous solution, and the mixture is heated, preferably at a temperature in the range of from 30 to 100° C., more preferably from 35 to 90° C., more preferably from 40 to 80° C., more preferably from 45 to 75° C., more preferably from 50 to 70° C., and more preferably from 55 to 65° C. According to a second alternative, it is preferred that in (H) the zeolitic material is added to the aqueous solution, and the mixture is treated at a temperature in the range of from 5 to 40° C., more preferably from 10 to 35° C., more preferably from 15 to 30° C., more preferably from 17 to 25° C., more preferably from 19 to 23° C., and more preferably from 20 to 22° C.

In the case where the process comprises the organotemplate-free synthetic process including (H), (I), optionally (J), and optionally (K) as disclosed above, no particular restriction applies as regards the conditions, e. g. the period, at which the mixture is treated in (H). It is preferred that in (H) the mixture is treated for a period in the range of from 0.1 to 10 h, more preferably from 0.1 to 7 h, more preferably from 0.5 to 5 h, more preferably from 0.5 to 4.5 h, more preferably from 1 to 4 h, more preferably from 1 to 3.5 h, more preferably from 1.5 to 3 h, and more preferably from 1.5 to 2.5 h.

In the case where the process comprises the organotemplate-free synthetic process including at least (A), (B), (C), optionally (D), and optionally (E) as disclosed above, no particular restriction applies as regards the conditions, e. g. the temperature, at which drying in (E) and/or (G) and/or (K), preferably in (E), (G) and (K), is conducted. It is preferred that drying in (E) and/or (G) and/or (K), preferably in (E), (G) and (K), is conducted at a temperature in the range of from 80 to 200° C., more preferably from 90 to 180° C., more preferably from 100 to 160° C., more preferably from 110 to 140° C., and more preferably from 115 to 130° C.

In the case where the process comprises the organotemplate-free synthetic process including at least (A), (B), (C), optionally (D), and optionally (E) as disclosed above, no particular restriction applies as regards the conditions, e. g. the period, at which drying in (E) and/or (G) and/or (K), preferably in (E), (G) and (K), is conducted. It is preferred that drying in (E) and/or (G) and/or (K), preferably in (E), (G) and (K), is conducted for a period in the range of from 1 to 120 h, preferably from 5 to 96 h, more preferably from 8 to 72 h, more preferably from 10 to 60 h, more preferably from 12 to 48 h, more preferably from 14 to 42 h, more preferably from 16 to 36 h, more preferably from 18 to 30 h, more preferably from 20 to 24 h, and more preferably from 21 to 23 h.

Therefore, it is particularly preferred that in the case where the process comprises the organotemplate-free synthetic process including at least (A), (B), (C), optionally (D), and optionally (E) as disclosed above drying in (E) and/or (G) and/or (K), preferably in (E), (G) and (K), is conducted at a temperature in the range of from 80 to 200° C., more preferably from 90 to 180° C., more preferably from 100 to 160° C., more preferably from 110 to 140° C., and more preferably from 115 to 130° C., and that drying in (E) and/or (G) and/or (K), preferably in (E), (G) and (K), is conducted for a period in the range of from 1 to 120 h, preferably from 5 to 96 h, more preferably from 8 to 72 h, more preferably from 10 to 60 h, more preferably from 12 to 48 h, more preferably from 14 to 42 h, more preferably from 16 to 36 h, more preferably from 18 to 30 h, more preferably from 20 to 24 h, and more preferably from 21 to 23 h.

In the case where the process comprises the organotemplate-free synthetic process including at least (F) and (G) as disclosed above, no particular restriction applies as regards the conditions, e. g. the temperature, of the calcining in (G) and/or (K), if (K) is applicable, at which calcining is conducted. It is preferred that the calcining in (G) and/or (K), if (K) is applicable, more preferably in (G) is conducted at a temperature in the range of from 250 to 1,000° C., preferably from 300 to 900° C., more preferably from 350 to 850° C., more preferably from 400 to 800° C., more preferably from 450 to 750° C., more preferably from 500 to 700° C., and more preferably from 550 to 650° C.

In the case where the process comprises the organotemplate-free synthetic process including at least (F) and (G) as disclosed above, no particular restriction applies as regards the conditions, e. g. the period, of the calcining in (G) and/or (K), if (K) is applicable, at which calcining is conducted. It is preferred that the calcining in (G) and/or (K), if (K) is applicable, more preferably in (G) is conducted for a period in the range of from 0.5 to 36 h, more preferably from 1 to 24 h, more preferably from 1.5 to 18 h, more preferably from 2 to 12 h, more preferably from 2.5 to 9 h, more preferably from 3 to 7 h, more preferably from 3.5 to 6.5 h, more preferably from 4 to 6 h, and more preferably from 4.5 to 5.5 h.

Therefore, it is particularly preferred that in the case where the process comprises the organotemplate-free synthetic process including at least (F) and (G) as disclosed above the calcining in (G) and/or (K), if (K) is applicable, more preferably in (G) is conducted at a temperature in the range of from 250 to 1,000° C., preferably from 300 to 900° C., more preferably from 350 to 850° C., more preferably from 400 to 800° C., more preferably from 450 to 750° C., more preferably from 500 to 700° C., and more preferably from 550 to 650° C., and that the calcining in (G) and/or (K), if (K) is applicable, more preferably in (G) is conducted for a period in the range of from 0.5 to 36 h, more preferably from 1 to 24 h, more preferably from 1.5 to 18 h, more preferably from 2 to 12 h, more preferably from 2.5 to 9 h, more preferably from 3 to 7 h, more preferably from 3.5 to 6.5 h, more preferably from 4 to 6 h, and more preferably from 4.5 to 5.5 h.

In the case where the process comprises the organotemplate-free synthetic process comprising at least (A) and (B) as disclosed above, no particular restriction applies as regards the physical and/or chemical nature of the zeolitic material having a BEA-type framework structure formed in (B). It is preferred that the zeolitic material having a BEA-type framework structure formed in (B) comprises zeolite beta, wherein preferably the zeolitic material having a BEA-type framework structure formed in (B) is zeolite beta.

In the case where the process comprises the organotemplate-free synthetic process comprising at least (A) and (B) as disclosed above, no particular restriction applies as regards the physical and/or chemical nature of the seed crystals contained in the mixture prepared in (A) and crystallized in (B). It is preferred that the seed crystals contained in the mixture prepared in (A) and crystallized in (B) comprise a zeolitic material having a BEA-type framework structure, more preferably zeolite beta, and more preferably a zeolitic material having a BEA-type framework structure as obtainable and/or obtained according to the organotemplate-free synthetic process for the preparation of the zeolitic material having a BEA-type framework structure as disclosed herein.

The present invention is further illustrated by the following embodiments and combinations of embodiments as indicated by the respective dependencies and back-references. In particular, it is noted that in each instance where a combination of embodiments is mentioned as a range, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4". Thus, the present invention includes the following embodiments, wherein these include the specific combinations of embodiments as indicated by the respective interdependencies defined therein:

1. A process for the production of an aromatic compound comprising:
   (1) preparing a mixture (M1) comprising ethylene and a compound of formula (I)

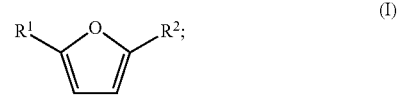

(I)

(2) feeding the mixture (M1) into a reactor containing a catalyst, said catalyst comprising a zeolitic material having a BEA-type framework structure;
   (3) contacting the mixture (M1) with the catalyst in the reactor for reacting at least a portion of the mixture (M1) to an aromatic compound of formula (II)

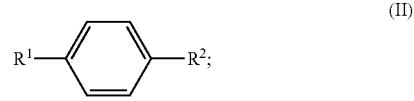

(II)

(4) collecting a reacted mixture (M2) containing the aromatic compound of formula (II) from the reactor;
   wherein independently from one another $R^1$ and $R^2$ stand for H or for substituted or unsubstituted ($C_1$-$C_3$)alkyl, preferably for H or for substituted or unsubstituted ($C_1$-$C_2$)alkyl, more preferably for H or for substituted or unsubstituted methyl, and more preferably for H or for unsubstituted methyl, and
   wherein the zeolitic material having a BEA-type framework structure comprised in the catalyst is obtainable and/or obtained according to an organotemplate-free synthetic process.

2. The process of embodiment 1, wherein the zeolitic material having a BEA-type framework structure displays an X-ray diffraction pattern comprising at least the following reflections:

| Intensity (%) | Diffraction angle 2 θ/° [Cu K(alpha 1)] |
| --- | --- |
| [12-32] | [21.79-21.99] |
| 100 | [22.28-22.48] |

-continued

| Intensity (%) | Diffraction angle<br>2 θ/° [Cu K(alpha 1)] |
|---|---|
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2 θ range of the X-ray powder diffraction pattern, and wherein the BEA-type framework structure comprises $SiO_2$ and $X_2O_3$, wherein X is a trivalent element.

3. The process of embodiment 1 or 2, wherein independently from one another $R^1$ and $R^2$ stand for substituted or unsubstituted $(C_1-C_3)$alkyl, preferably for substituted or unsubstituted $(C_1-C_2)$alkyl, more preferably for substituted or unsubstituted methyl, more preferably for unsubstituted methyl.

4. The process of any of embodiments 1 to 3, wherein $R^1$ stands for H and $R^2$ stands for substituted or unsubstituted $(C_1-C_3)$alkyl, preferably for substituted or unsubstituted $(C_1-C_2)$alkyl, more preferably for substituted or unsubstituted methyl, and more preferably for unsubstituted methyl.

5. The process of any of embodiments 1 to 4, wherein the compound of formula (I) is selected from the group consisting of substituted or unsubstituted furan, 2-methylfuran, 2,5-dimethylfuran, and mixtures of two or more thereof, preferably from the group consisting of unsubstituted furan, 2-methylfuran, 2,5-dimethylfuran, and mixtures of two or more thereof, wherein more preferably the compound of formula (I) is 2-methylfuran and/or 2,5-dimethylfuran, preferably 2,5-dimethylfuran.

6. The process of any of embodiments 1 to 5, wherein the ethylene:compound of formula (I) molar ratio of ethylene to the compound of formula (I) in the mixture (M1) prepared in (1) and reacted in (3) is in the range of from 0.01 to 1.5, preferably from 0.05 to 1, more preferably from 0.08 to 0.7, more preferably from 0.1 to 0.5, more preferably from 0.12 to 0.3, more preferably from 0.14 to 0.2, and more preferably from 0.16 to 0.18.

7. The process of any of embodiments 1 to 6, wherein the mixture (M1) prepared in (1) and reacted in (3) contains 5 wt.-% or less of water based on 100 wt.-% of the compound of formula (I), preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of water based on 100 wt.-% of the compound of formula (I).

8. The process of any of embodiments 1 to 7, wherein the mixture (M1) prepared in (1) and reacted in (3) further contains a solvent system, wherein the solvent system preferably comprises one or more solvents selected from the group consisting of butane, pentane, hexane, heptane, octane, nonane, decane, and mixtures of two or more thereof, preferably from the group consisting of pentane, hexane, heptane, octane, nonane, and mixtures of two or more thereof, more preferably from the group consisting of hexane, heptane, octane, and mixtures of two or more thereof, wherein more preferably the solvent system comprises heptane, wherein more preferably the solvent system consists of heptane.

9. The process of embodiment 8, wherein the mixture (M1) prepared in (1) and reacted in (3) contains a solution of the compound of formula (I) in the solvent system, wherein the concentration of the compound of formula (I) in the solvent system is in the range of from 0.1 to 5 M, 0.5 to 3 M, more preferably from 1 to 2.5 M, more preferably from 1.3 to 2 M, more preferably from 1.4 to 1.7 M, and more preferably from 1.5 to 1.6 M.

10. The process of any of embodiments 1 to 9, wherein the partial pressure of ethylene in the reactor in which the mixture (M1) is fed in (2) and contacted with the catalyst in (3) is in the range of from 0.5 to 15 when measured at 25° C., preferably from 0.5 to 15 MPa, more preferably from 1 to 10 MPa, more preferably from 2 to 8 MPa, more preferably from 2.5 to 6 MPa, more preferably from 3 to 5 MPa, and more preferably from 3.5 to 4.5 MPa.

11. The process of any of embodiments 1 to 10, wherein the compound of formula (I) and/or ethylene, preferably the compound of formula (I) and ethylene are derived from biomass.

12. The process of any of embodiments 1 to 11, wherein in (2) and (3) the zeolitic material having a BEA-type framework structure comprised in the catalyst is in the H-form.

13. The process of any of embodiments 1 to 12, wherein in (2) and (3) the zeolitic material having a BEA-type framework structure comprised in the catalyst contains 5 wt.-% or less of a metal AM calculated as the element and based on 100 wt.-% of $SO_2$ contained in the framework structure of the zeolitic material having a BEA-type framework structure, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt. % or less, and more preferably 0.0001 wt.-% or less of a metal AM calculated as the element and based on 100 wt.-% of $SiO_2$ contained in the framework structure of the zeolitic material having a BEA-type framework structure, wherein the metal AM stands for Na, preferably for Na and K, more preferably for alkali metals, and more preferably for alkali and alkaline earth metals.

14. The process of any of embodiments 1 to 13, wherein in (2) and (3) the zeolitic material having a BEA-type framework structure comprised in the catalyst contains 5 wt.-% or less of a metal TM calculated as the element and based on 100 wt.-% of $SiO_2$ contained in the framework structure of the zeolitic material having a BEA-type framework structure, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt. % or less, and more preferably 0.0001 wt.-% or less of a metal TM calculated as the element and based on 100 wt.-% of $SiO_2$ contained in the framework structure of the zeolitic material having a BEA-type framework structure, wherein the metal TM stands for Pt, Pd, Rh, and Ir, and preferably stands for transition metal elements of groups 3-12.

15. The process of any of embodiments 1 to 14, wherein in (2) and (3) the catalyst in the reactor contains 5 wt.-% or less of a metal AM calculated as the element and based on 100 wt.-% of the catalyst, preferably 1 wt.-% or less, more preferably 0.5 wt.-% or less, more preferably 0.1 wt.-% or less, more preferably 0.05 wt.-% or less, more preferably 0.01 wt. % or less, more preferably 0.005 wt.-% or less, more preferably 0.001 wt.-% or less, more preferably 0.0005 wt.-% or less, and more preferably 0.0001 wt.-% or less of a metal AM calculated as the element and based on 100 wt.-% of the catalyst,
wherein the metal AM stands for Na, preferably for Na and K, more preferably for alkali metals, and more preferably for alkali and alkaline earth metals.

16. The process of any of embodiments 1 to 15, wherein in (2) and (3) the catalyst contained in the reactor contains 5 wt.-% or less of a metal TM calculated as the element and based on 100 wt.-% of the catalyst, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal TM calculated as the element and based on 100 wt.-% of the catalyst,
wherein the metal TM stands for Pt, Pd, Rh, and Ir, and preferably stands for transition metal elements of groups 3-12.

17. The process of any of embodiments 1 to 16, wherein in (2) and (3) the zeolitic material having a BEA-type framework structure comprised in the catalyst contains 5 wt. % or less of phosphorous calculated as the element and based on 100 wt.-% of $SiO_2$ contained in the framework structure of the zeolitic material having a BEA-type framework structure, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt. % or less, and more preferably 0.0001 wt.-% or less of phosphorous calculated as the element and based on 100 wt.-% of $SiO_2$ contained in the framework structure of the zeolitic material having a BEA-type framework structure.

18. The process of any of embodiments 1 to 17, wherein in (2) and (3) the catalyst contains 5 wt. % or less of phosphorous calculated as the element and based on 100 wt.-% of the catalyst, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal AM calculated as the element and based on 100 wt.-% of the catalyst.

19. The process of any of embodiments 1 to 18, wherein the contacting of the mixture (M1) with the catalyst in (3) is conducted at a temperature in the range of from 150 to 350° C., preferably from 200 to 330° C., more preferably from 230 to 320° C., more preferably from 250 to 315° C., more preferably from 270 to 310° C., more preferably from 280 to 305° C., and more preferably in the range of from 290 to 300° C.

20. The process of any of embodiments 1 to 19, wherein the duration of the contacting of the mixture (M1) with the catalyst in (3) is in the range of from 0.5 to 70 h, preferably from 1 to 50 h, more preferably from 3 to 40 h, more preferably from 5 to 35 h, more preferably from 10 to 30 h, more preferably from 15 to 25 h, more preferably from 18 to 23 h, and more preferably in the range of from 19 to 21 h.

21. The process of any of embodiments 1 to 20, wherein the contacting of the mixture (M1) with the catalyst in (3) and the collecting of the reacted mixture (M2) in (4) is conducted in a continuous mode and/or in a batch mode, preferably in a batch mode.

22. The process of any of embodiments 1 to 21, wherein the process is conducted in a continuous mode and/or in a batch mode, preferably in a batch mode.

23. The process of any of embodiments 1 to 22, wherein the process further comprises:
(5) separating the compound of formula (II) from the reacted mixture (M2) for obtaining a mixture (M3) containing unreacted compound of formula (I) and/or unreacted ethylene.

24. The process of embodiment 23, wherein the process further comprises:
(6) recycling the mixture (M3) containing unreacted compound of formula (I) and/or unreacted ethylene to (1).

25. The process of any of embodiments 1 to 24, wherein the zeolitic material having a BEA-type framework structure comprised in the catalyst displays a $SiO_2:X_2O_3$ molar ratio in the range of from 10 to 200, preferably from 15 to 150, more preferably from 20 to 100, more preferably from 25 to 70, more preferably from 30 to 65, more preferably from 35 to 60, more preferably from 38 to 55, more preferably from 40 to 50, and more preferably from 42 to 46, wherein preferably the $SiO_2:X_2O_3$ molar ratio of the framework structure is determined from elemental analysis or from the $^{29}Si$ MAS NMR of the zeolitic material, preferably from the $^{29}Si$ MAS NMR of the zeolitic material.

26. The process of any of embodiments 1 to 25, wherein the trivalent element X of the zeolitic material having a BEA-type framework structure comprised in the catalyst is selected from the group consisting of Al, B, In, Ga, and a mixture of two or more thereof, X preferably being Al.

27. The process of any of embodiments 1 to 26, wherein the zeolitic material having a BEA-type framework structure comprised in the catalyst displays and amount of Bronsted acid sites (BA) in the range of from 100 to 900 µmol/g, preferably from 150 to 700 µmol/g, more preferably from 200 to 650 µmol/g, more preferably from 350 to 600 µmol/g, more preferably from 380 to 550 µmol/g, more preferably from 410 to 500 µmol/g, more preferably from 430 to 470 µmol/g, and more preferably from 445 to 450 µmol/g, wherein the amount of Bronsted acid sites is determined according to the temperature programmed desorption of ammonia ($NH_3$-TPD) or according to $^{31}P$ MAS NMR using trimethylphosphine oxide.

28. The process of any of embodiments 1 to 27, wherein the zeolitic material having a BEA-type framework structure comprised in the catalyst displays an amount of Lewis acid sites (LA) in the range of from 100 to 350 µmol/g, preferably from 110 to 300 µmol/g, more preferably from 120 to 280 µmol/g, more preferably from 140 to 260 µmol/g, more preferably from 150 to 240 µmol/g, more preferably from 160 to 220 µmol/g, more preferably from 170 to 200 µmol/g, and more preferably from 180 to 190 µmol/g,
wherein the amount of Lewis acid sites is determined according to the temperature programmed desorption of ammonia ($NH_3$-TPD) or according to $^{31}P$ MAS NMR using trimethylphosphine oxide.

29. The process of any of embodiments 1 to 28, wherein the ratio BA:LA of the amount of Bronsted acid sites (BA) to the amount of Lewis acid sites (LA) displayed by the zeolitic material having a BEA-type framework structure comprised in the catalyst is in the range of from 0.5 to 8, preferably from 1 to 5, more preferably from 1.3 to 4, more preferably from 1.6 to 3.4, more preferably from 1.8 to 3, more preferably from 2.0 to 2.7, more preferably from 2.2 to 2.6, and more preferably from 2.3 to 2.5,
wherein the amount of Bronsted and Lewis acid sites is respectively determined according to the temperature programmed desorption of ammonia ($NH_3$-TPD) or according to $^{31}P$ MAS NMR using trimethylphosphine oxide.

30. The process of any of embodiments 1 to 29, wherein the BET surface area of the zeolitic material having a BEA-type framework structure comprised in the catalyst as determined according to ISO 9277:2010 is in the range of from 350 to 800 $m^2/g$, preferably from 400 to 700 $m^2/g$, more preferably from 430 to 650 $m^2/g$, more preferably from 450 to 600 $m^2/g$, more preferably from 460 to 550 $m^2/g$, more preferably from 470 to 530 $m^2/g$, more preferably from 480 to 520 $m^2/g$, and more preferably from 490 to 510 $m^2/g$.

31. The process of any of embodiments 1 to 30, wherein the total pore volume of the zeolitic material having a BEA-type framework structure comprised in the catalyst as determined by nitrogen adsorption from the BJH method is in the range of from 0.3 to 0.5 $cm^3/g$, preferably from 0.31 to 0.45 $cm^3/g$, more preferably from 0.32 to 0.42 $cm^3/g$, more preferably from 0.33 to 0.4 $cm^3/g$, more preferably from 0.34 to 0.39 $cm^3/g$, more preferably from 0.35 to 0.38 $cm^3/g$, and more preferably from 0.36 to 0.37 $cm^3/g$,
wherein the total pore volume is preferably determined according to DIN 66134.

32. The process of any of embodiments 1 to 31, the organotemplate-free synthetic process comprising
(A) preparing a mixture comprising one or more sources for $SiO_2$, one or more sources for $X_2O_3$, and seed crystals, the seed crystals comprising one or more zeolitic materials having a BEA-type framework structure;
(B) crystallizing the mixture obtained in (A) for obtaining a zeolitic material having a BEA-type framework structure;
wherein X is a trivalent element, and
wherein the mixture prepared in (A) and crystallized in (B) does not contain an organotemplate as structure-directing agent.

33. The process of embodiment 32, wherein the mixture prepared in (A) and crystallized in (B) contains 5 wt.-% or less of carbon calculated as the element and based on 100 wt.-% of $SiO_2$ contained in the mixture, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of carbon calculated as the element and based on 100 wt.-% of $SiO_2$ contained in the mixture.

34. The process of embodiment 32 or 33, wherein the zeolitic material having a BEA-type framework structure obtained in (B) comprises one or more alkali metals M, wherein M is preferably selected from the group consisting of Li, Na, K, Cs, and combinations of two or more thereof, more preferably from the group consisting of Li, Na, K, and combinations of two or more thereof, wherein more preferably the alkali metal M is Na and/or K, more preferably Na.

35. The process of embodiment 34, wherein the molar ratio $M:SiO_2$ in the mixture prepared in (A) and crystallized in (B) is in the range of from 0.05 to 5, preferably from 0.1 to 2, more preferably from 0.3 to 1, more preferably from 0.4 to 0.8, more preferably from 0.45 to 0.7, more preferably from 0.5 to 0.65, and more preferably from 0.55 to 0.6.

36. The process of any of embodiments 32 to 35, wherein the one or more sources for $SiO_2$ contained in the mixture prepared in (A) and crystallized in (B) comprises one or more silicates, preferably one or more alkali metal silicates, wherein the alkali metal is preferably selected from the group consisting of Li, Na, K, Rb, and Cs, wherein more preferably the alkali metal is Na and/or K, and wherein more preferably the alkali metal is Na, wherein more preferably the one or more sources for $SiO_2$ contained in the mixture prepared in (A) and crystallized in (B) comprises water glass, preferably sodium and/or potassium silicate, more preferably sodium silicate.

37. The process of any of embodiment 36, wherein the one or more sources for $SiO_2$ contained in the mixture prepared in (A) and crystallized in (B) further comprises one or more silicas, preferably one or more silica hydrosols and/or one or more colloidal silicas, and more preferably one or more colloidal silicas.

38. The process of any of embodiments 32 to 37, wherein X is selected from the group consisting of Al, B, In, Ga, and a mixture of two or more thereof, X preferably being Al.

39. The process of any of embodiments 32 to 38, wherein the one or more sources for $X_2O_3$ contained in the mixture prepared in (A) and crystallized in (B) comprises one or more aluminate salts, preferably an aluminate of an alkali metal, wherein the alkali metal is preferably selected from the group consisting of Li, Na, K, Rb, and Cs, wherein more preferably the alkali metal is Na and/or K, and wherein more preferably the alkali metal is Na.

40. The process of any of embodiments 32 to 39, wherein the molar ratio $SiO_2:X_2O_3$ of the mixture prepared in (A) and crystallized in (B) is in the range of from 1 to 200, preferably from 5 to 100, more preferably from 10 to 50, more preferably from 15 to 40, more preferably from 20 to 30, more preferably from 23 to 25, and more preferably from 23.5 to 24.

41. The process of any of embodiments 32 to 40, wherein the amount of seed crystals comprised in the mixture prepared in (A) and crystallized in (B) is in the range of from 0.1 to 30 wt.-% based on 100 wt.-% of the one or more sources of $SiO_2$ in the mixture, calculated as $SiO_2$, preferably from 0.5 to 20 wt.-%, more preferably from 1 to 10 wt.-%, more preferably from 1.5 to 5 wt.-%, more preferably from 2 to 4 wt.-%, and more preferably from 2.5 to 3.5 wt.-%.

42. The process of any of embodiments 32 to 41, wherein the mixture prepared in (A) and crystallized in (B) further comprises one or more solvents, wherein said one or more solvents preferably comprises water, more preferably deionized water, wherein more preferably water is employed as the solvent further comprised in the mixture prepared in (A) and crystallized in (B), preferably deionized water.

43. The process of embodiment 42, wherein the molar ratio $H_2O:SiO_2$ of the mixture prepared in (A) and crystallized in (B) is in the range of from 5 to 100, preferably from 10 to 50, more preferably from 13 to 30, more preferably from 15 to 20, and more preferably from 17 to 18.

44. The process of any of embodiments 32 to 43, wherein the crystallization in (B) involves heating of the mixture, preferably at a temperature in the range of from 80 to 200° C., more preferably from 90 to 180° C., more preferably from 100 to 160° C., more preferably from 110 to 140° C., and more preferably from 115 to 130° C.

45. The process of any of embodiments 32 to 44, wherein the crystallization in (B) is conducted under autogenous pressure, preferably under solvothermal conditions, and more preferably under hydrothermal conditions.

46. The process of embodiment 44 or 45, wherein in (B) the mixture is heated for a period in the range of from 5 to 200 h, preferably from 20 to 160 h, more preferably from 60 to 140 h, and more preferably from 100 to 130 h.

47. The process of any of embodiments 32 to 46, wherein the organotemplate-free synthetic process for the preparation of the zeolitic material having a BEA-type framework structure further comprises
    (C) isolating the zeolitic material having a BEA-type framework structure obtained in (B), preferably by filtration; and
    (D) optionally washing the zeolitic material having a BEA-type framework structure obtained in (B) or (C), preferably in (C); and/or,
    (E) optionally drying the zeolitic material having a BEA-type framework structure obtained in (B), (C) or (D), preferably in (D);
    wherein steps (C) and/or (D) and/or (E) can be conducted in any order, and
    wherein one or more of said steps is preferably repeated one or more times.

48. The process of embodiment 47, wherein the organotemplate-free synthetic process for the preparation of the zeolitic material having a BEA-type framework structure further comprises
    (F) exchanging one or more of the ionic non-framework elements contained in the zeolitic material having a BEA-type framework structure obtained in (C), (D), or (E), preferably in (E), against $H^+$ and/or $NH_4^+$, preferably against $NH_4^+$; and/or, preferably and
    (G) drying and/or calcining, preferably drying and calcining the zeolitic material having a BEA-type framework structure obtained in (C), (D), (E), or (F);
    wherein steps (F) and/or (G) is preferably repeated one or more times, preferably one to three times, more preferably once or twice, and more preferably once.

49. The process of embodiment 47 or 48, wherein the organotemplate-free synthetic process for the preparation of the zeolitic material having a BEA-type framework structure further comprises
    (H) treating the zeolitic material having a BEA-type framework structure obtained in (C), (D), (E), (F), or (G), preferably in (G), with an aqueous solution having a pH of at most 5; and
    (I) isolating the zeolitic material having a BEA-type framework structure obtained in (H), preferably by filtration; and/or,
    (J) optionally washing the zeolitic material having a BEA-type framework structure obtained in (H) or (I), preferably in (I); and/or,
    (K) optionally drying and/or calcining, preferably drying the zeolitic material having a BEA-type framework structure obtained in (H), (I), or (J), preferably in (J);
    wherein the steps (I) and/or (J) and/or (K) can be conducted in any order, and
    wherein one or more of said steps is preferably repeated one or more times, preferably one to three times, more preferably once or twice, and more preferably once.

50. The process of embodiment 49, wherein the pH of the aqueous solution used for treating the zeolitic material in (H) has a pH in the range of from −1.5 to 3, preferably of from −1.2 to 2, more preferably of from −1 to 1.5, more preferably of from −0.8 to 1, more preferably of from −0.6 to 0.7, more preferably of from −0.5 to 0.5, more preferably of from −0.3 to 0.3, more preferably of from −0.2 to 0.2, and more preferably of from −0.1 to 0.1.

51. The process of embodiment 49 or 50, wherein in (H) the zeolitic material is treated with an aqueous solution of a mineral acid, wherein the concentration of the mineral acid in the solution is in the range of from 0.05 to 4 M, preferably from 0.1 to 3 M, more preferably from 0.2 to 2.5 M, more preferably from 0.4 to 2 M, more preferably from 0.6 to 1.5 M, more preferably from 0.8 to 1.2 M, and more preferably from 0.9 to 1.1 M.

52. The process of embodiment 51, wherein the mineral acid is selected from the group consisting of HF, HCl, HBr, $HNO_3$, $H_3PO_4$, $H_2SO_4$, $H_3BO_3$, $HClO_4$, and mixtures of two or more thereof, preferably from the group consisting of HCl, HBr, $HNO_3$, $H_2SO_4$, $HClO_4$, and mixtures of two or more thereof, more preferably from the group consisting of HCl, $HNO_3$, $H_2SO_4$, and mixtures of two or more thereof, wherein more preferably the mineral acid is HCl and/or $HNO_3$, preferably $HNO_3$.

53. The process of any of embodiments 49 to 52, wherein in (H) the zeolitic material is added to the aqueous solution, and the mixture is heated, preferably at a temperature in the range of from 30 to 100° C., more preferably from 35 to 90° C., more preferably from 40 to 80° C., more preferably from 45 to 75° C., more preferably from 50 to 70° C., and more preferably from 55 to 65° C.

54. The process of any of embodiments 49 to 52, wherein in (H) the zeolitic material is added to the aqueous solution, and the mixture is treated at a temperature in the range of from 5 to 40° C., more preferably from 10 to 35° C., more preferably from 15 to 30° C., more preferably from 17 to 25° C., more preferably from 19 to 23° C., and more preferably from 20 to 22° C.

55. The process of any of embodiments 49 to 54, wherein in (H) the mixture is treated for a period in the range of from 0.1 to 10 h, preferably from 0.1 to 7 h, more preferably from 0.5 to 5 h, more preferably from 0.5 to 4.5 h, more preferably from 1 to 4 h, more preferably from 1 to 3.5 h, more preferably from 1.5 to 3 h, and more preferably from 1.5 to 2.5 h.

56. The process of any of embodiments 47 to 55, wherein drying in (E) and/or (G) and/or (K), preferably in (E), (G) and (K), is conducted at a temperature in the range of from 80 to 200° C., more preferably from 90 to 180° C., more preferably from 100 to 160° C., more preferably from 110 to 140° C., and more preferably from 115 to 130° C.

57. The process of any of embodiments 47 to 56, wherein drying in (E) and/or (G) and/or (K), preferably in (E), (G) and (K) is conducted for a period in the range of from 1 to 120 h, preferably from 5 to 96 h, more preferably from 8 to 72 h, more preferably from 10 to 60 h, more preferably from 12 to 48 h, more preferably from 14 to 42 h, more preferably from 16 to 36 h, more preferably from 18 to 30 h, more preferably from 20 to 24 h, and more preferably from 21 to 23 h.

58. The process of any of embodiments 48 to 57, wherein calcining in (G) and/or (K), preferably in (G) is conducted at a temperature in the range of from 250 to 1,000° C., preferably from 300 to 900° C., more preferably from 350 to 850° C., more preferably from 400 to 800° C., more preferably from 450 to 750° C., more preferably from 500 to 700° C., and more preferably from 550 to 650° C.
59. The process of any of embodiments 48 to 58, wherein calcining in (G) and/or (K), preferably in (G) is conducted for a period in the range of from 0.5 to 36 h, more preferably from 1 to 24 h, more preferably from 1.5 to 18 h, more preferably from 2 to 12 h, more preferably from 2.5 to 9 h, more preferably from 3 to 7 h, more preferably from 3.5 to 6.5 h, more preferably from 4 to 6 h, and more preferably from 4.5 to 5.5 h.
60. The process of any of embodiments 32 to 59, wherein the zeolitic material having a BEA-type framework structure formed in (B) comprises zeolite beta, wherein preferably the zeolitic material having a BEA-type framework structure formed in (B) is zeolite beta.
61. The process of any of embodiments 32 to 60, wherein the seed crystals contained in the mixture prepared in (A) and crystallized in (B) comprise a zeolitic material having a BEA-type framework structure, preferably zeolite beta, and more preferably a zeolitic material having a BEA-type framework structure as obtainable and/or obtained according to the organotemplate-free synthetic process for the preparation of the zeolitic material having a BEA-type framework structure as defined in any of claims 32 to 59.

EXPERIMENTAL SECTION

Determination of Porosity

Figure 1:
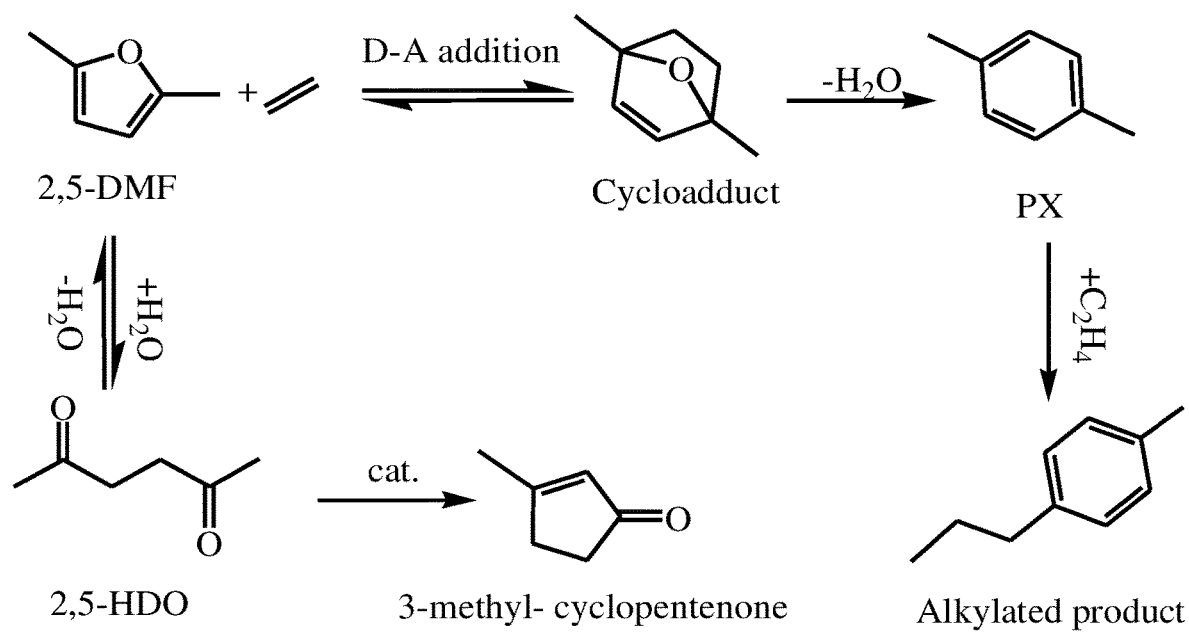
FIG. 1 displays the reaction scheme of 2,5-dimethylfuran (2,5-DMF) via Diels-Alder cycloaddition of ethylene to a cycloadduct intermediate, which the converts to p-xylene by elimination of water. The main side reactions to 3-methyl-cyclopentanone as well as the further alkylation to 1-n-propyl-4-methylbenzene are also displayed.

Surface areas, pore volumes and pore size distributions were determined by the $N_2$ adsorption/desorption experiments at −196° C. on a Micromeritics ASAP-2020 analyzer. Before each measurement the samples were outgassed at 400° C. and below $10^{-3}$ Pa for 6 h.

Temperature Programmed Desorption of Ammonia ($NH_3$-TPD) and Determination of Acidity $NH_3$ temperature-programmed desorption ($NH_3$-TPD) was carried out using a chemisorption analyzer (FINETECH, Finesorb 3010C, China) to detect the effluent gases using TCD. Before the measurements, the samples were pretreated in He stream at 500° C. and cooled down to the desired temperature. 5000 ppm $NH_3$ in He (100 ml/min) was introduced at 100° C. for 0.5 h, followed by He purging for 1.5 h, then the temperature was ramped from 100 to 700° C. at a rate of 10° C./min.

After deconvoluting the $NH_3$ temperature-programmed desorption (TPD) profiles, all samples showed three desorption peaks centered at ca. 200° C. (low temperature), 250° C. (middle temperature) and 340° C. (high temperature), respectively. The latter two peaks could be roughly attributed to $NH_3$ desorption on strong and weak Bronsted acid sites (BA), while the low-temperature peak could be assigned to $NH_3$ desorption on Lewis acid sites (LA). Based thereon, the respective amounts of Bronsted (BA) and Lewis (LA) acid sites as well as the B/L ratios were calculated through the integration of desorption signals.

$^{31}P$ MAS NMR Measurements and Determination of Acidity Using TMPO

All solid-state magic-angle-spinning (MAS) NMR experiments were carried out on an Agilent DD2-500 MHz spectrometer. $^{31}P$ MAS NMR single-pulse spectra were measured at 202.3 MHz with a speed of 14 kHz, $\pi/4$ excitation pulse of 1.2 µs and recycle delay of 10 s. The chemical shifts were referenced to 85% $H_3PO_4$.

To get more insights into the acid amount and strength of H-Beta zeolites with different Si/Al ratios, $^{31}P$ MAS NMR experiments are conducted, which is an effective tool to investigate the acidic properties using trimethylphosphine oxide (TMPO) as a probe molecule. Not only the acid sites types (Bronsted acid or Lewis acid) can be distinguished, $^{31}P$-TMPO MAS NMR approach is also more useful for discriminating the Bronsted acid strength of zeolite catalysts and capable of covering the whole range from weak, medium, strong to superacidity.

For the quantitative measurement of acidity, all samples were weighed, and the spectra were calibrated by measuring a known amount of $(NH_4)_2HPO_4$ performed in the same conditions except for the longer pulse delay of 90 s. For the adsorption of trimethylphosphine oxide (TMPO, 99%, Alfa) during preparation of the samples for the measurement, the samples were firstly subjected to a full dehydration under vacuum for 20 h. Subsequently, a known amount of TMPO dissolved in anhydrous $CH_2Cl_2$ was introduced into a vessel containing the dehydrated solid samples in a $N_2$ atmosphere, followed by removal of the $CH_2Cl_2$ solvent by evacuation at ca. 50° C. To ensure a uniform adsorption of probe molecules in the zeolites, they were further subjected to thermal treatment at 165° C. for 1 h. Finally, the samples were transferred into an NMR rotor and then sealed by a gas-tight endcap in the $N_2$ glove box.

After deconvolution of the $^{31}P$ MAS NMR, seven peaks appeared from the low to high field. Besides the physisorbed TMPO at around 43 ppm, the $^{31}P$ NMR chemical shifts from 50 to 84 ppm are ascribed to chemical adsorbed TMPO on Bronsted or Lewis acid sites. More specifically, the peaks at ca. 83, 69 and 55-62 ppm are assigned to TMPO adsorbed on the strongest, medium-strength and weakest Bronsted acid sites, respectively, while those at 65 and 50 ppm are ascribed to TMPO adsorbed on the Lewis acid sites. Based on said classification, the total amount of Bronsted (BA) and Lewis (LA) acid sites were quantified the B/L ratios were calculated based on the obtained values.

$^{29}$Si MAS NMR Measurements

All solid-state magic-angle-spinning (MAS) NMR experiments were carried out on an Agilent DD2-500 MHz spectrometer. $^{29}$Si MAS NMR spectra were collected at 99.3 MHz using a 6 mm MAS probe with a speed of 4 kHz, 400 scans and recycle delay of 4 s. Chemical shifts were referenced to 4,4-dimethyl-4-silapentane sulfonate sodium (DSS).

The Si/Al molar ratios in the framework of the respective materials was determined by deconvolution of the corresponding $^{29}$Si MAS NMR spectra.

Reference Example 1: Organotemplate-Free Synthesis of H-BEA 12.693 kg of distilled water were placed in a 60 L autoclave with stirring means. 0.955 kg of NaAlO$_2$ were dissolved in 5 L of distilled water and added to the water in the autoclave while stirring. 21.447 kg of sodium waterglass (26 wt.-% SiO$_2$, 8 wt.-% Na$_2$O, and 66 wt.-% H$_2$O) were then added under stirring, wherein the viscosity of the mixture sharply increased and then decreased again. 3.762 kg of Ludox® AS40 (40 wt.-% SiO$_2$ and 60 wt.-% H$_2$O) were then added and the resulting gel was stirred at 200 rpm for 3 h, followed by addition of a suspension of 0.717 kg of zeolite Beta seeds (commercially available from Zeolyst International, Valley Forge, Pa. 19482, USA, under the tradename CP814C, CAS Registry Number 1318-02-1, which was converted to the H-form by calcination at 550° C. for 5 h, wherein a heat ramp of 1° C./min was used for attaining the calcination temperature) in 1 L of distilled water under stirring at 100 rpm. The resulting mixture thus contained an aluminosilicate gel with a molar ratio of 1.00 SiO$_2$:0.0422 Al$_2$O$_3$:0.291 Na$_2$O: 17.50 H$_2$O. The reaction mixture was heated under stirring at 100 rpm in 3 h to a temperature of 120° C. using a constant heat ramp, wherein said temperature was then maintained under the same stirring speed for 60 h. After having let the reaction mixture cool to room temperature, the solid was separated by filtration, repeatedly washed with distilled water and then dried at 120° C. for 16 h for affording Na-zeolite beta. X-ray diffraction of the product confirmed the BEA-type framework structure of the crystalline material obtained. The resulting white crystalline material displayed a crystallinity of 93% compared to the crystallinity of the zeolite beta seed material (CP814C from Zeolyst) in the 2° Theta range od 18 to 25°.

1,000 g of distilled water were placed in a 2 L reaction vessel. 125 g ammonium nitrate and 125 g of Na-zeolite beta obtained according to Reference Example 1 were then added to the mixture over a funnel, which was then rinsed with 125 g of distilled water. The resulting suspension was then heated to 80° C. and kept at this temperature under continuous stirring for 2 h. The solid was filtered, and the filter cake was then washed with distilled water until the conductivity of the wash water was below 20 microSiemens/cm. The filter cake was dried over night at 120° C. affording 138.5 g of zeolite beta in its ammonium form. This procedure was repeated with a further 125 g of Na-zeolite beta from Reference Examples 1, affording a further 131.5 g of zeolite beta in its ammonium form. Finally, a calcination step of both batches at 500° C. for 5 h (heat ramp 2 K/min) afforded 236 g of zeolite beta in its H-form.

1,000 g of distilled water were placed in a 2 L reaction vessel. 118 g ammonium nitrate and 118 g of H-zeolite beta obtained from the first ammonium ion-exchange procedure were then added to the mixture over a funnel, which was then rinsed with 118 g of distilled water. The resulting suspension was then heated to 80° C. and kept at this temperature under continuous stirring for 2 h. The solid was filtered, and the filter cake was then washed with distilled water until the conductivity of the wash water was below 10 microSiemens/cm. The filter cake was dried over night at 120° C. affording 111 g of zeolite beta in its ammonium form. This procedure was repeated with 125 g of ammonium nitrate and a further 125 g of H-zeolite beta obtained from the first ammonium ion-exchange procedure, thus affording a further 110 g of zeolite beta in its ammonium form. The samples of H-zeolite beta were united, and a sample of 65 g thereof was subject to a calcination step at 750° C. for 5 h (heat ramp 2 K/min) affording 59.5 g of zeolite beta in its H-form. The Si:Al molar ratio of the H-zeolite beta as determined from $^{29}$Si MAS NMR spectra was 7.

Reference Example 2: Dealumination of H-BEA Obtained from Organotemplate-Free Synthesis 1,250 ml of a 1 M solution of nitric acid were placed in a beaker equipped with a stirrer. 25 g of H-zeolite beta obtained from Reference Example 1 were added and the mixture was stirred for 2 h at room temperature. The solid was the filtered off and washed with distilled water until the conductivity of the wash water was 165 microSiemens/cm. The solid was then dried over night at 120° C. to afford 23.7 g of zeolite beta, wherein elemental analysis afforded a Si:Al weight ratio of 40:2.6. The Si:Al molar ratio of the dealuminated zeolite beta as determined from $^{29}$Si MAS NMR spectra was 22.

Reference Example 3: Dealumination of H-BEA Obtained from Organotemplate-Free Synthesis 1,219 ml of a 1 M solution of nitric acid were placed in a beaker equipped with a stirrer. 24.38 g of H-zeolite beta obtained from Reference Example 1 were added and the mixture was stirred for 5 h at room temperature. The solid was the filtered off and washed with distilled water until the conductivity of the wash water was 65 microSiemens/cm. The solid was then dried over night at 120° C. to afford 21.4 g of zeolite beta, wherein elemental analysis afforded a Si:Al weight ratio of 40:2.1. The Si:Al molar ratio of the dealuminated zeolite beta as determined from $^{29}$Si MAS NMR spectra was 36.

Example 1: Synthesis of Aromatic Compounds

The catalytic conversion of 2,5-dimethyl furan, 2-methylfuran or furan with ethylene was carried out in a 50 ml stainless steel autoclave. Before reactions, the autoclave was purged by nitrogen, then 0.3 g of H-Beta zeolite was placed in the reactor, and the desired amounts of 2,5-dimethyl furan, 2-methylfuran or furan with solvent were transferred into the autoclave. More specifically, a 1.56 M solution of the respective compound in heptane was employed. The reactor was then pressurized with ethylene gas, and the mixture was stirred at 1000 rpm with a mechanical stirrer to ensure facile mass transfer in the system, and heated up to the final temperature. In the reaction, the molar the ratio of ethylene to 2,5-dimethyl furan was 0.18, of ethylene to 2-methyl furan was 0.18, and of ethylene to furan was 0.16.

After reactions, the liquid products and solid catalyst were separated by centrifugation. The products were analyzed using the gas chromatograph (Shimadzu, GC-2014C) equipped with a 30 m HP-5 capillary column and the flame ionization detector. The products were identified based on the retention times and response factors of the standard chemicals, and quantified using a known amount of n-decane as the external standard. The products were further identified by GC/MS (Agilent, HP6890/5973MSD) equipped with a 30 m HP-5 MS column.

For comparison, commercial zeolite Beta with Si/Al=19 from organotemplate mediated synthesis (CP814C, $NH_4^+$-form, Zeolyst) was converted to the $H^+$-form by calcination at 550° C. for 4 h and subsequently used for the comparative test runs. The Si:Al molar ratio of the commercial zeolite beta as determined from $^{29}Si$ MAS NMR spectra was 19.

The characteristics of the zeolite beta catalysts used in the testing experiments are displayed in Table 1. In particular, the molar Si:Al ratios as determined from the Si MAS NMR spectra, the ratio BA:LA of the amount of Bronsted acid sites (BA) to the amount of Lewis acid sites (LA) determined by the temperature programmed desorption of ammonia ($NH_3$-TPD) and according to $^{31}P$ MAS NMR using trimethylphosphine oxide, respectively, the absolute amounts of Bronsted acid sites and Lewis acid sites according to $NH_3$-TPD, and the BET surface area and total pore volume are shown.

TABLE 1

Characteristics of the zeolite beta catalysts used in the testing experiments.

| Catalyst | Si/Al ratio | BA/LA from $^{31}P$ MAS NMR | Bronsted acid [µmol/g] | Lewis acid [µmol/g] | BA/LA from $NH_3$-TPD | BET surface area [m²/g] | pore volume [cm³/g] |
|---|---|---|---|---|---|---|---|
| Ref. Ex. 1 | 7 | 7.0 | 956 | 110 | 8.7 | 449 | 0.31 |
| Commercial | 19 | 4.0 | 527 | 136 | 4.0 | 520 | 0.36 |
| Ref. Ex. 2 | 22 | 2.3 | 448 | 185 | 2.4 | 500 | 0.36 |
| Ref. Ex. 3 | 36 | 3.0 | 289 | 106 | 2.7 | 548 | 0.38 |

Figure 4:
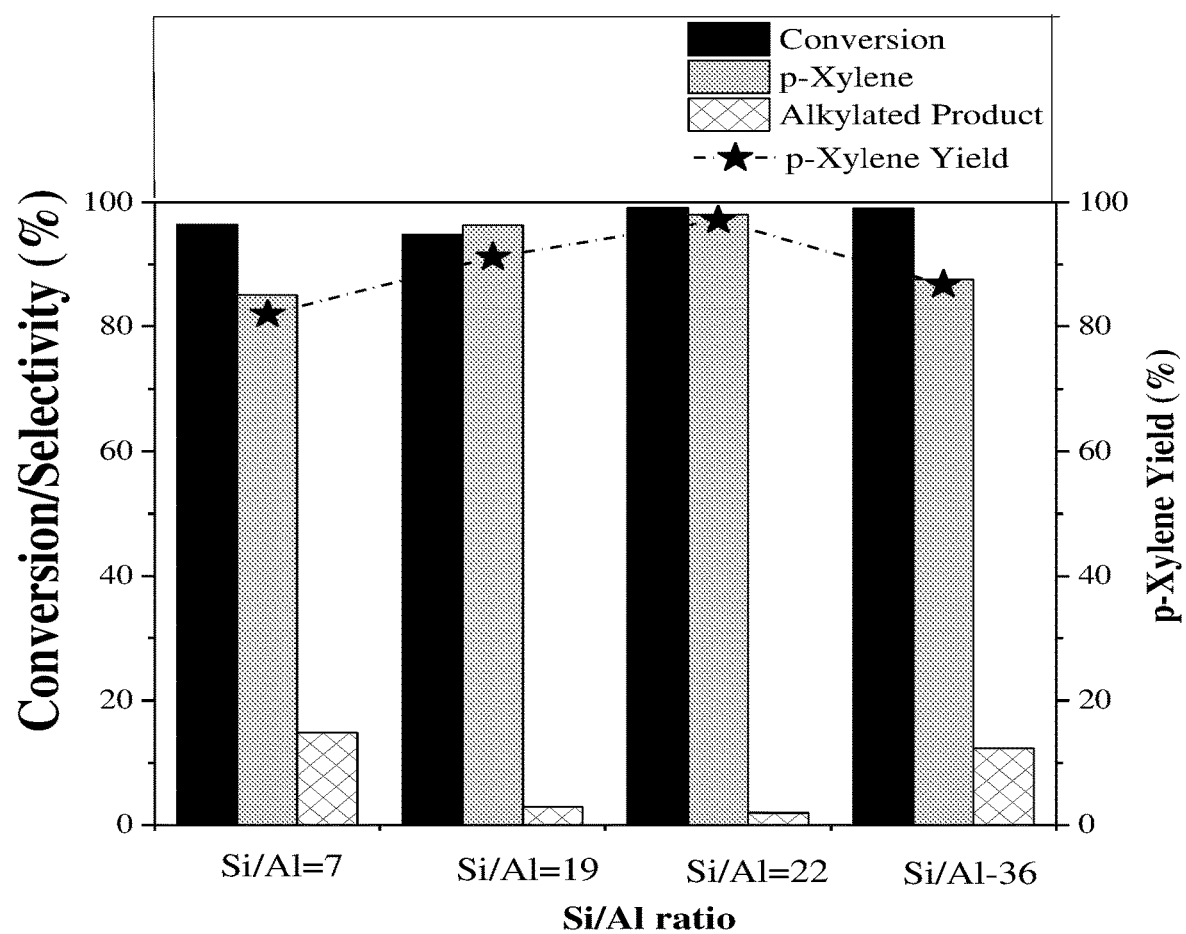
FIG. 4 displays the reaction products and selectivities in the conversion of 2,5-dimethylfuran and ethylene of zeolite beta catalysts according to Reference Example 1 (Si/Al=7), Reference Example 2 (Si/Al=22), Reference Example 3 (Si/Al=36), and a commercial zeolite beta (Si/Al=19). In the figure, the conversion, the selectivities towards p-xylene and the alkylated product 1-n-propyl-4-methylbenzene, and the yield in p-xylene (indicated by "★") are displayed in %.

The results from comparative testing of the different zeolite beta catalysts in the reaction of 2,5-dimethyl furan with ethylene are displayed in FIG. 4. The reaction was conducted at 300° C. for 20 h, wherein prior to the reaction, the reactor was pressurized with ethylene to afford an initial pressure of 4.0 MPa prior to heating. Thus, as may be taken from the results, it has quite unexpectedly been found that the conversion over zeolite beta as obtained from organotemplate free synthesis is substantially higher than for commercial zeolite beta obtained from templated synthesis. In particular, as may be taken from the results, it has quite surprisingly been found that the higher conversion rates are not linked to the Si/Al molar ratio, but that the improved results of the catalysts used in the inventive process result from the fact that they are obtained from an organotemplate-free synthetic process. Thus, as may be taken from the results obtained using the zeolite beta samples obtained from organotemplate-free synthesis displaying Si/Al molar ratios of 7 and 22, respectively, both display substantially higher conversion rates than commercial zeolite beta as obtained from templated synthesis having an Si/Al molar ratio of 19, i.e. lying in between the aforementioned Si/Al molar ratios.

Figure 2:
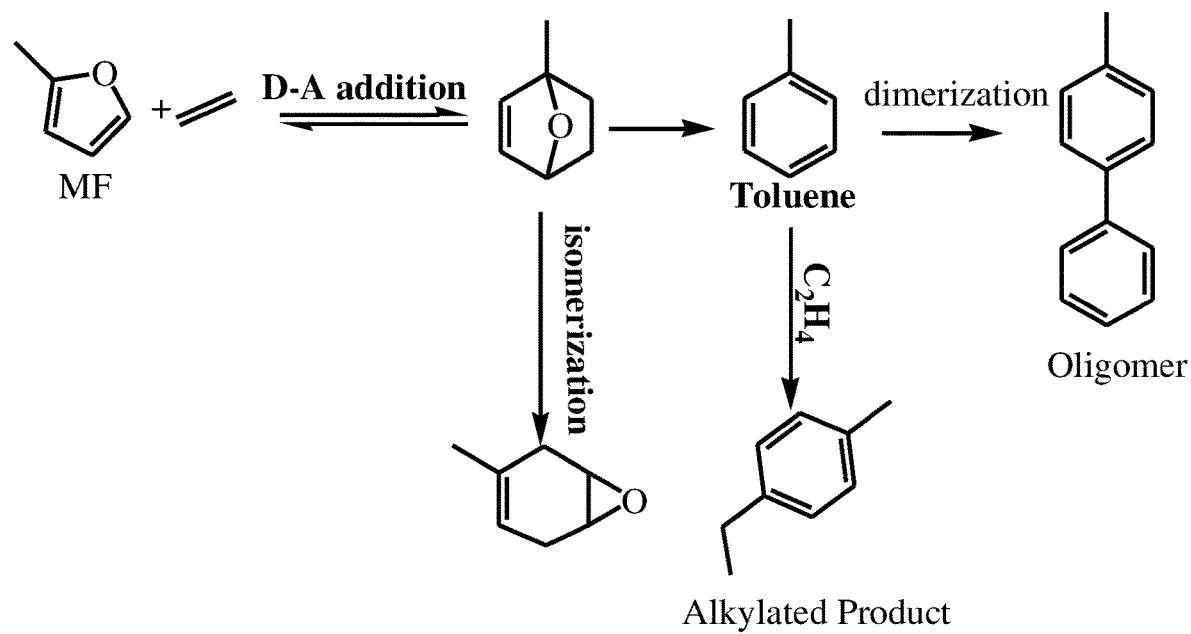
FIG. 2 displays the reaction scheme of 2-methylfuran via Diels-Alder cycloaddition of ethylene to a cycloadduct intermediate, which the converts to toluene by elimination of water. The main side reactions to the oligomer, to the epoxide via isomerization of the cycloadduct, to 1-ethyl-4-methylbenzene via further alkylation of the product as well as to the oligomer via dimerization are also displayed.
Figure 3:
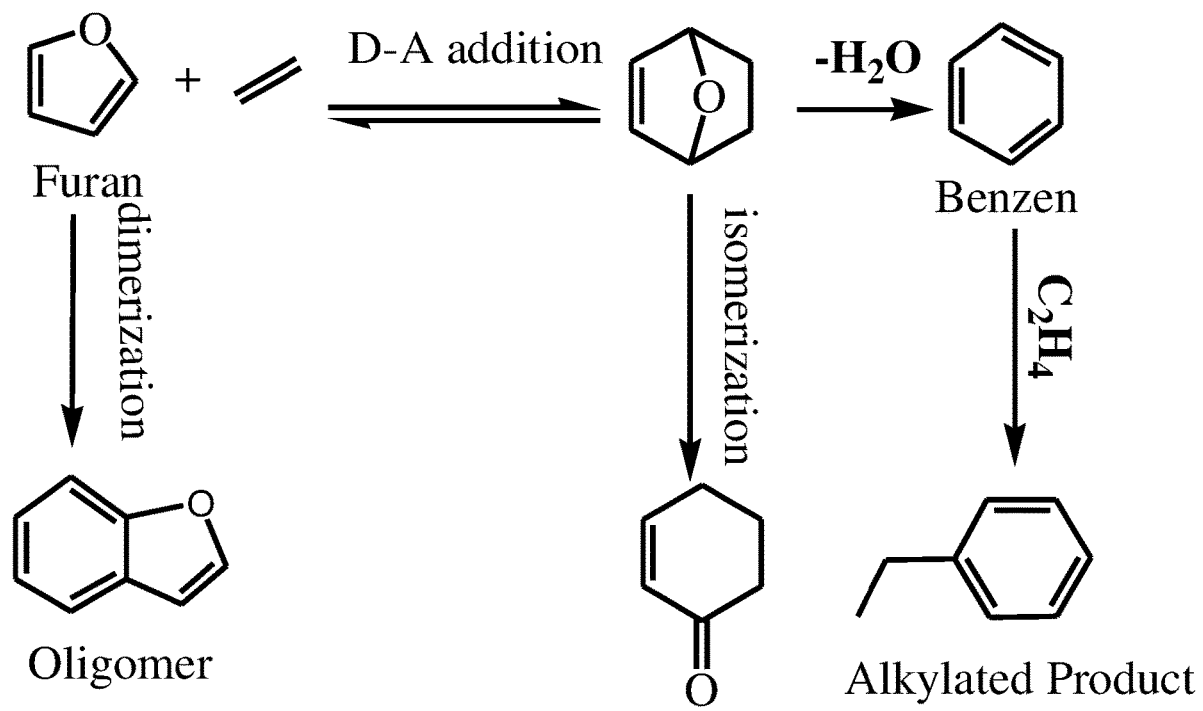
FIG. 3 displays the reaction scheme of furan via Diels-Alder cycloaddition of ethylene to a cycloadduct intermediate, which the converts to benzene by elimination of water. The main side reactions to the oligomer via dimerization, to the ketone via isomerization of the cycloadduct as well as the further alkylation to ethylbenzene are also displayed.
Figure 5:
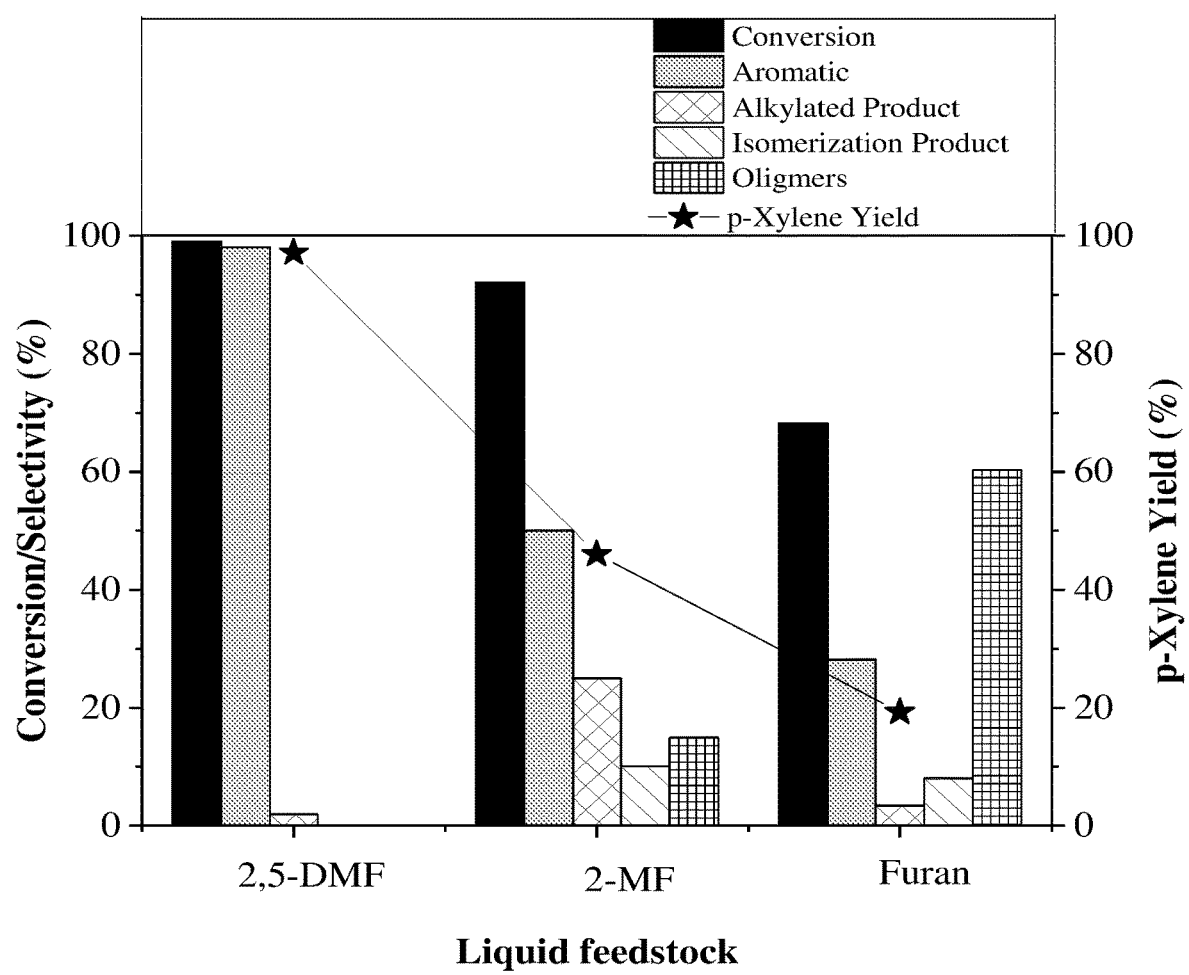
FIG. 5 displays the reaction products and selectivities in the conversion of ethylene and 2,5-dimethyl furan (2,5-DMF), 2-methylfuran (2-MF), and furan, respectively, over a zeolite beta catalyst according to Reference Example 2 (Si/Al=22). In the figure, the conversion, the selectivities towards p-xylene and the side products (alkylated and isomerized side products as well as oligomers), and the yield in p-xylene (indicated by "★") are displayed in %.

In addition to the aforementioned testing, zeolite beta from Reference Example 2 was used in the reaction of ethylene with 2,5-dimethyl furan, 2-methylfuran, and furan, respectively, the results of which are displayed in FIG. 5. The reaction pathways to the desired aromatic products of the Diels-Alder cycloaddition and subsequent elimination of water as well as to the main side products are displayed in FIGS. 1-3, respectively. As may be taken from the results displayed in FIG. 5, the conversion and the selectivity of the reaction towards the desired product is almost 100%, respectively, in the reaction of 2,5-dimethylfuran, whereas the conversion rate and selectivities considerably decrease when reacting ethylene with 2-methylfuran and furan, respectively.

LIST OF CITED DOCUMENTS

US 2013/0245316 A1
Ni, L. et al. *ChemSusChem* 2017, 10, 2394
Chang, C.-C. et al. *Green Chem.* 2014, 16, 585
Cho, H. J. et al. *ChemCatChem* 2017, 9, 398

What is claimed is:

1. A process for the production of an aromatic compound, comprising:

feeding a mixture (M1) comprising ethylene and a compound of formula (I),

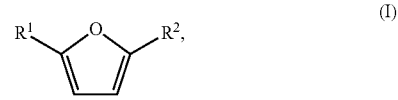
(I)

into a reactor comprising a catalyst, the catalyst comprising a zeolitic material having a BEA-type framework structure;

contacting the mixture (M1) with the catalyst in the reactor for reacting at least a portion of the mixture (M1) to an aromatic compound of formula (II),

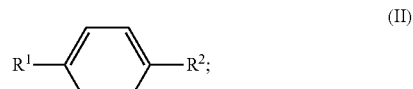
(II)

and collecting a reacted mixture (M2) comprising the aromatic compound of formula (II) from the reactor;

wherein R$^1$ and R$^2$ are each independently selected from the group consisting of H, a substituted (C$_1$-C$_3$)alkyl, and an unsubstituted (C$_1$-C$_3$)alkyl, and wherein the zeolitic material having a BEA-type framework structure is obtained by an organotemplate-free synthetic process.

2. The process of claim 1, wherein the zeolitic material having a BEA-type framework structure displays an X-ray diffraction pattern comprising at least the following reflections:

| Intensity (%) | Diffraction angle 2θ/° [Cu K(alpha 1)] |
|---|---|
| [12-32] | [21.79-21.99] |
| 100 | [22.28-22.48] |
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2θ range of the X-ray powder diffraction pattern, and wherein the BEA-type framework structure comprises SiO$_2$ and X$_2$O$_3$, wherein X is a trivalent element.

3. The process of claim 1, wherein the compound of formula (I) is at least one selected from the group consisting of a substituted furan, an unsubstituted furan, a 2-methylfuran, a 2,5-dimethylfuran, and a mixture of two or more thereof.

4. The process of claim 1, wherein the mixture (M1) further comprises a solvent system.

5. The process of claim 1, wherein the compound of formula (I) and/or ethylene are derived from biomass.

6. The process of claim 1, wherein the zeolitic material having a BEA-type framework structure is in the H-form.

7. The process of claim 1, wherein the zeolitic material having a BEA-type framework structure comprises 5 wt.-% or less of Na calculated as the element and based on 100 wt.-% of SiO$_2$ contained in the framework structure of the zeolitic material having a BEA-type framework structure.

8. The process of claim 1, wherein the zeolitic material having a BEA-type framework structure comprises 5 wt.-% or less of a metal TM calculated as the element and based on 100 wt.-% of SiO$_2$ contained in the framework structure of the zeolitic material having a BEA-type framework structure, wherein the metal TM stands for at least one selected from the group consisting of Pt, Pd, Rh, and Ir.

9. The process of claim 1, wherein the zeolitic material having a BEA-type framework structure comprises 5 wt. % or less of phosphorous calculated as the element and based on 100 wt.-% of SiO$_2$ contained in the framework structure of the zeolitic material having a BEA-type framework structure.

10. The process of claim 1, wherein the contacting of the mixture (M1) with the catalyst is conducted at a temperature in the range of from 150 to 350° C.

11. The process of claim 1, which is conducted in a continuous mode and/or in a batch mode.

12. The process of claim 1, wherein the trivalent element X of the zeolitic material having a BEA-type framework structure is at least one selected from the group consisting of Al, B, In, Ga, and a mixture of two or more thereof.

13. The process of claim 1, wherein the ratio BA:LA of the amount of Bronsted acid sites (BA) to the amount of Lewis acid sites (LA) displayed by the zeolitic material having a BEA-type framework structure is in the range of from 0.5 to 8, wherein the amount of Bronsted and Lewis acid sites is determined according to the temperature programmed desorption of ammonia (NH3-TPD) or according to $^{31}$P MAS NMR using trimethylphosphine oxide.

14. The process of claim 1, wherein the zeolitic material having a BEA-type framework structure is obtained by an organotemplate-free synthetic process comprising:

crystallizing a mixture comprising one or more sources for SiO$_2$, one or more sources for X$_2$O$_3$, and seed crystals to obtain the zeolitic material having a BEA-type framework structure;

wherein the seed crystals comprise one or more zeolitic materials having a BEA-type framework structure, wherein X is a trivalent element, and wherein the mixture does not contain an organotemplate as a structure-directing agent.

15. The process of claim 14, wherein the mixture comprises 5 wt.-% or less of carbon calculated as the element, based on 100 wt-% of SiO$_2$ contained in the mixture.

* * * * *